United States Patent
Yamada et al.

(10) Patent No.: US 10,020,158 B2
(45) Date of Patent: Jul. 10, 2018

(54) TRANSMITTING-TYPE TARGET AND X-RAY GENERATION TUBE PROVIDED WITH TRANSMITTING-TYPE TARGET

(71) Applicant: CANON KABUSHIKI KAISHA, Tokyo (JP)

(72) Inventors: Shuji Yamada, Atsugi (JP); Takeo Tsukamoto, Kawasaki (JP); Takao Ogura, Yokohama (JP); Tadayuki Yoshitake, Cambridge, MA (US); Yoichi Ikarashi, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 470 days.

(21) Appl. No.: 14/559,807

(22) Filed: Dec. 3, 2014

(65) Prior Publication Data

US 2015/0162161 A1    Jun. 11, 2015

(30) Foreign Application Priority Data

Dec. 6, 2013  (JP) .................................. 2013-253634
Dec. 6, 2013  (JP) .................................. 2013-253635
Sep. 10, 2014 (JP) .................................. 2014-184462

(51) Int. Cl.
| | |
|---|---|
| H01J 35/00 | (2006.01) |
| H01J 35/08 | (2006.01) |
| G01N 23/04 | (2018.01) |
| H01J 35/04 | (2006.01) |
| C23C 16/01 | (2006.01) |
| C23C 16/27 | (2006.01) |

(52) U.S. Cl.
CPC .............. *H01J 35/08* (2013.01); *C23C 16/01* (2013.01); *C23C 16/27* (2013.01); *G01N 23/04* (2013.01); *H01J 35/045* (2013.01); *H01J 2235/02* (2013.01); *H01J 2235/081* (2013.01); *H01J 2235/084* (2013.01); *H01J 2235/087* (2013.01); *H01J 2235/186* (2013.01)

(58) Field of Classification Search
CPC ...................... H01J 2235/081; H01J 2235/084
See application file for complete search history.

(56) References Cited

U.S. PATENT DOCUMENTS

| | | |
|---|---|---|
| 5,148,462 A | 9/1992 | Spitsyn et al. |
| 5,432,003 A | 7/1995 | Plano et al. |
| | (Continued) | |

FOREIGN PATENT DOCUMENTS

| | | |
|---|---|---|
| CN | 101395246 A | 3/2009 |
| JP | 2003-505845 A | 2/2003 |
| | (Continued) | |

*Primary Examiner* — Dani Fox
(74) *Attorney, Agent, or Firm* — Canon USA Inc., IP Division

(57) ABSTRACT

A transmissive-type target includes a target layer, and a transmissive substrate configured to support the target layer. The transmissive substrate has a pair of surfaces facing each other and is formed of polycrystalline diamond. In the transmissive substrate, one of the pair of surfaces includes polycrystalline diamond having a first average crystal grain diameter which is smaller than a second average crystal grain diameter of polycrystalline diamond included on the other surface opposing thereto. The target layer is supported by any one of the pair of surfaces.

24 Claims, 15 Drawing Sheets

(56) References Cited

U.S. PATENT DOCUMENTS

| | | | | |
|---|---|---|---|---|
| 6,118,853 A * | 9/2000 | Hansen | ............... | H01J 35/108 |
| | | | | 378/143 |
| 6,319,610 B1 * | 11/2001 | Zimmer | ............... | B24D 3/06 |
| | | | | 428/141 |
| 6,850,598 B1 * | 2/2005 | Fryda | ............... | H01J 35/10 |
| | | | | 378/140 |
| 2011/0142202 A1 * | 6/2011 | Brown | ............... | A61N 5/1049 |
| | | | | 378/65 |

FOREIGN PATENT DOCUMENTS

| | | | |
|---|---|---|---|
| JP | 2009-545840 | A | 12/2009 |
| JP | 2012-004060 | A | 1/2012 |
| JP | 2012-256444 | A | 12/2012 |
| JP | 2013-160637 | A | 8/2013 |
| WO | 2008/060671 | A2 | 5/2008 |
| WO | 2012/152661 | A1 | 11/2012 |

* cited by examiner

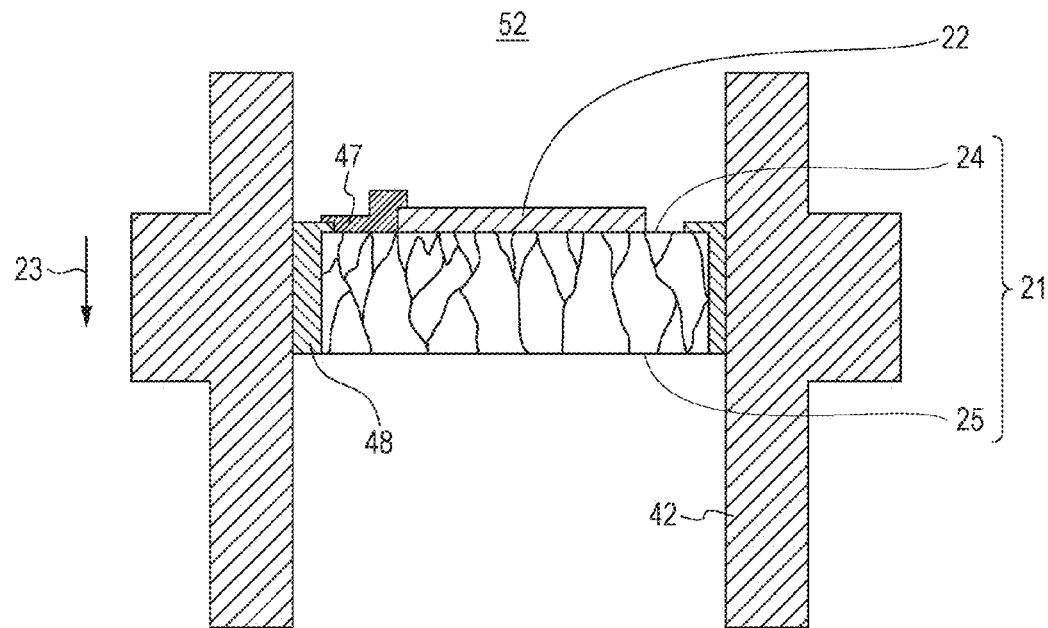
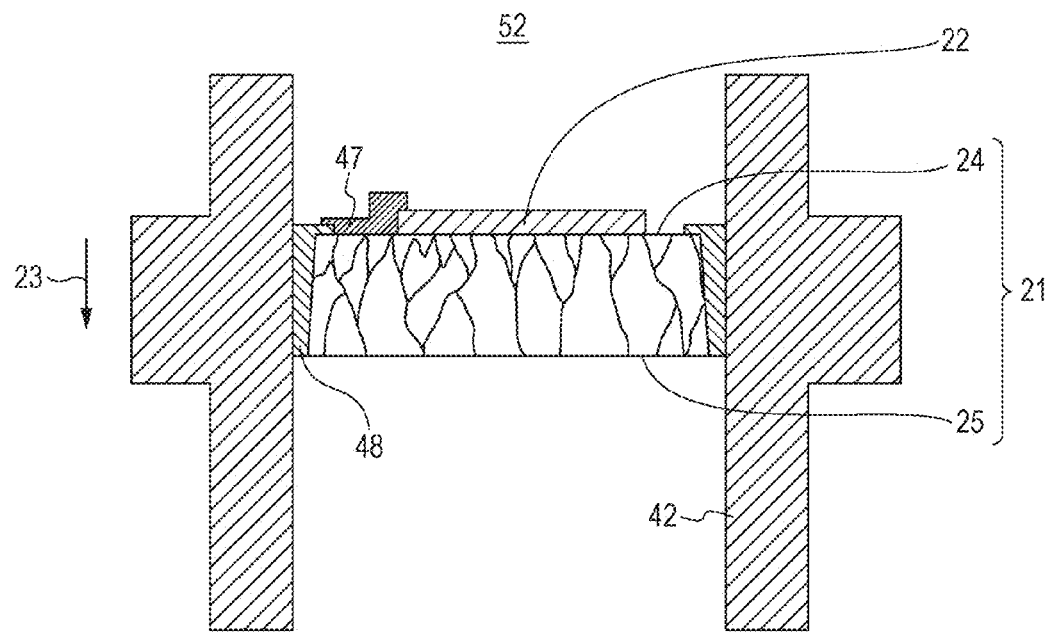

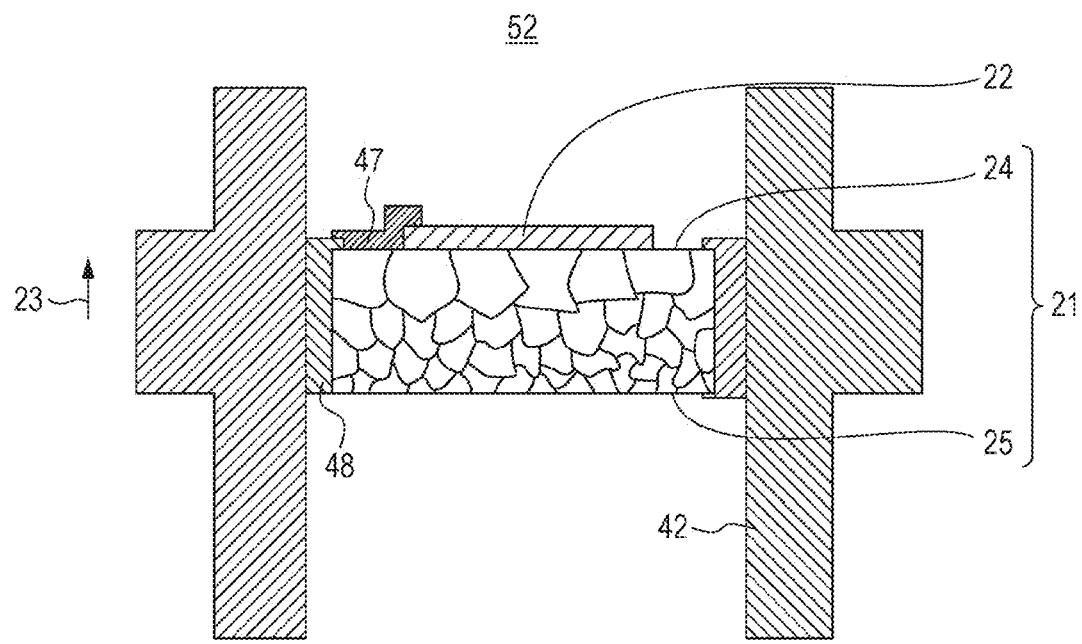
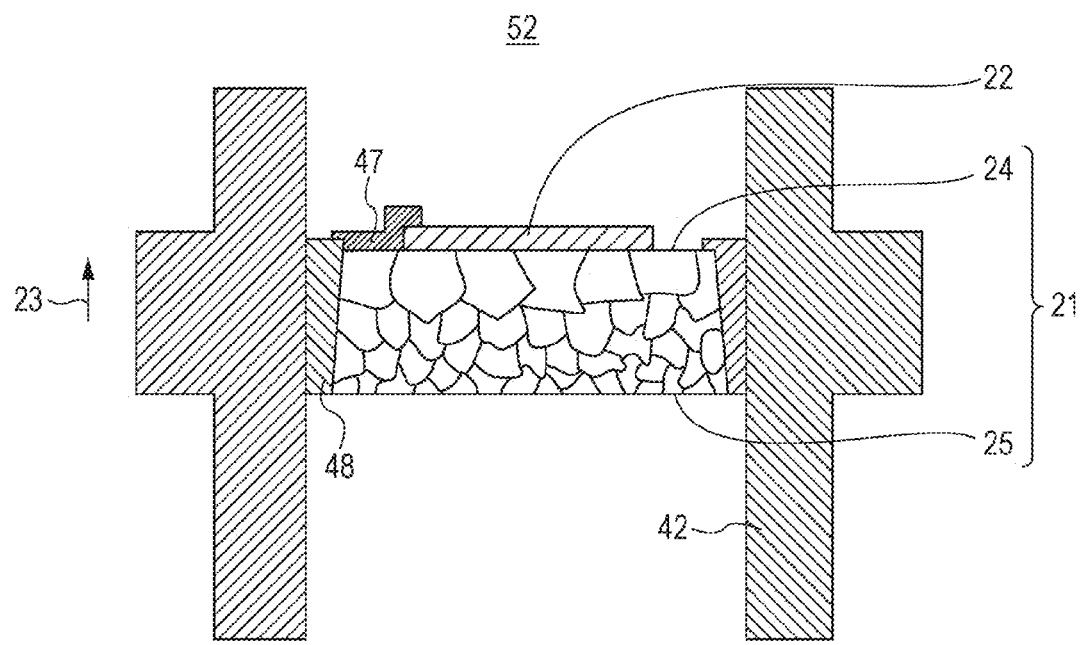

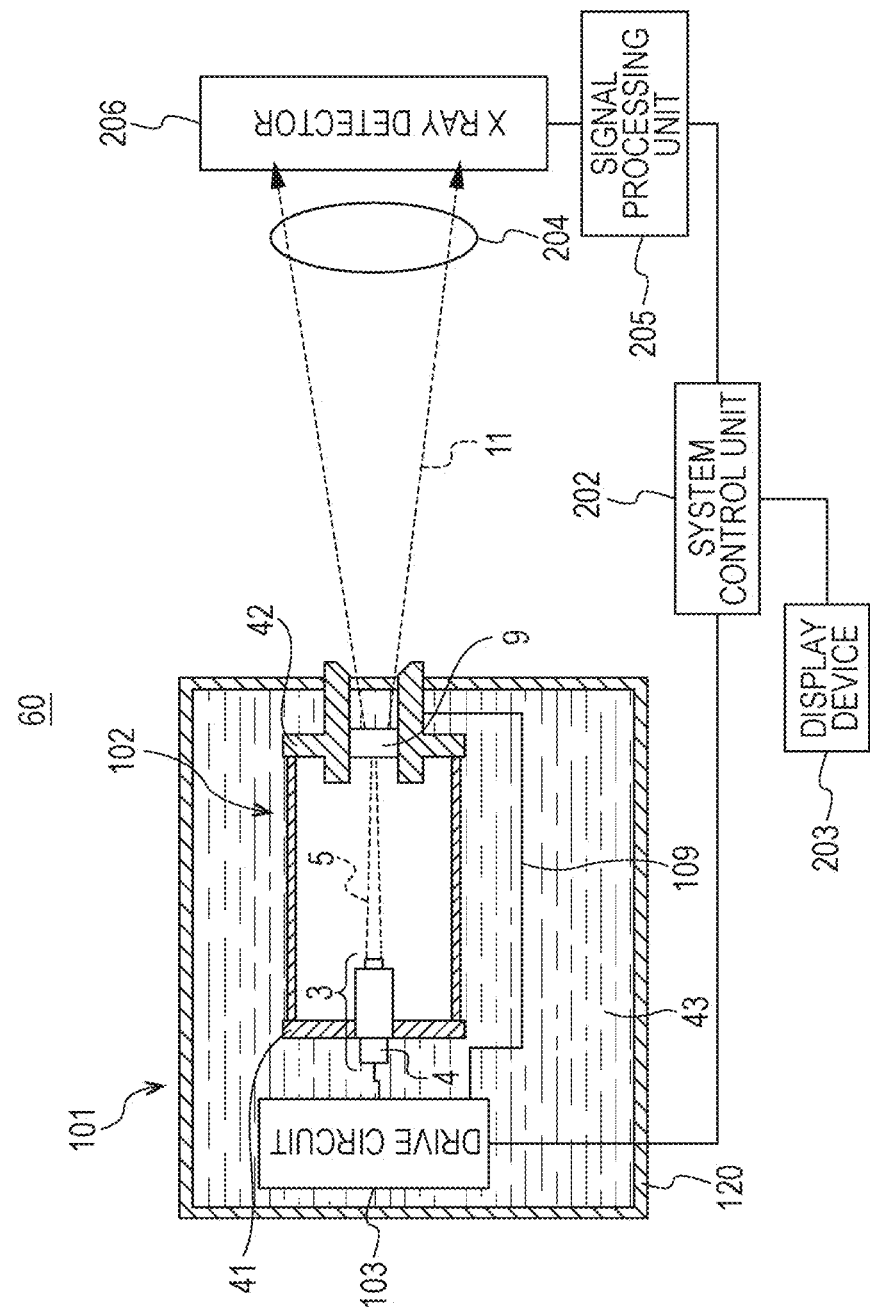

TRANSMITTING-TYPE TARGET AND X-RAY GENERATION TUBE PROVIDED WITH TRANSMITTING-TYPE TARGET

BACKGROUND OF THE INVENTION

Field of the Invention

This disclosure relates to an X-ray generation tube applicable to an imaging apparatus for medical diagnosis and non-destructive X-ray radiographing in a field of industrial apparatus. This disclosure specifically relates to a transmitting-type target applied to the X-ray generation tube.

Description of the Related Art

In an X-ray generation apparatus, enhancement of durability and improvement of maintenance reduction are required.

As one of main causes which determine the durability of the X-ray generation apparatus, heat-resistant properties of a target, which corresponds to an X-ray source is exemplified.

In the X-ray generation apparatus configured to irradiate a target with an electron beam and thereby generate X-ray radiation, an "X-ray generation efficiency" of the target is lower than 1%. Therefore, most of energy applied to the target is converted into heat. When "dissipation" of heat generated in the target is not sufficient, loss of adhesiveness of the target is caused by melting, evaporation, and thermal stress of the target itself, so that the heat-resistant property of the target is limited.

As a technique for improving the "X-ray generation efficiency" from the target, employing a transmitting-type target composed of a target layer of a thin-film form containing a heavy metal and a base material configured to transmit an X-ray and support the target layer is publicly known. Japanese Patent Application Publication No. JP 2009-545840 (also published as WO 2008060671) discloses a rotating anode transmitting-type target in which the "X-ray generation efficiency" is increased to 1.5 times or higher with respect to a rotating anode reflective target of the related art.

As a method of accelerating "heat dissipation" from the target to the outside, application of diamond as a base material configured to support a target layer of a laminated target is publicly known. U.S. Pat. No. 6,850,598 discloses enhancing heat dissipation properties and achieving a fine focal point by employing monocrystal diamond or polycrystalline diamond as a substrate configured to support a target layer formed of tungsten. Diamond has high heat-resistant property and high heat conductivity, and has high X-ray transmissivity, and hence is a preferable material as a base material for supporting the transmitting-type target.

SUMMARY OF THE INVENTION

Polycrystalline diamond has equivalent physical properties in thermal conductivity, heat-resistant property, and X-ray transmissivity as a transmissive substrate to be applied to the transmitting-type X-ray target in comparison with monocrystal diamond. Furthermore, the polycrystalline diamond includes advantages that the transmissive substrate having sizes on the order of millimeter may be supplied stably at low prices.

However, as a result of inspection by the present inventors, disadvantages in the generation of electric discharge or lowering of an anode current, or disadvantages in the generation of X-ray output variations was found in the transmitting-type target having the transmissive substrate formed of polycrystalline diamond as that described in U.S. Pat. No. 6,850,598.

The present disclosure describes a transmitting-type target provided with a transmissive substrate formed of polycrystalline diamond in which generation of electric discharge, lowering of an anode current, and X-ray output variations are alleviated. In addition, the present disclosure describes an X-ray generation tube, an X-ray generation apparatus, and an X-ray imaging system in which generation of electric discharge, lowering of an anode current, and X-ray output variations are alleviated with high reliability.

According to one aspect of the present invention, a transmitting-type target includes: a target layer, and a transmissive substrate configured to support the target layer. The transmissive substrate includes a first surface and a second surface facing each other and is formed of polycrystalline diamond. The first surface includes polycrystalline diamond having a first average crystal grain diameter which is smaller than a second average crystal grain diameter of polycrystalline diamond included in the second surface thereof, and the target layer is supported by either the first surface or the second surface.

Further features of the present invention will become apparent from the following description of exemplary embodiments with reference to the attached drawings.

BRIEF DESCRIPTION OF THE DRAWINGS

FIG. 2A is a configuration drawing illustrating an anode to which the transmitting-type target of the first embodiment disclosed here is applied.

FIG. 2B is a configuration drawing illustrating an anode to which the transmitting-type target of a modification thereof is applied.

FIG. 4A is a configuration drawing illustrating an anode to which the transmitting-type target of the second embodiment disclosed here is applied.

FIG. 4B is a configuration drawing illustrating an anode to which the transmitting-type target of a modification thereof is applied.

FIG. 5C is a schematic configuration drawing illustrating an X-ray imaging system provided with a transmitting-type target of an embodiment.

DESCRIPTION OF THE EMBODIMENTS

Embodiments of this disclosure will be described with reference to the drawings in detail. Dimensions, materials, shapes, and relative arrangement of components described in the embodiments are not intended to limit the scope of this disclosure.

Figure 5A:
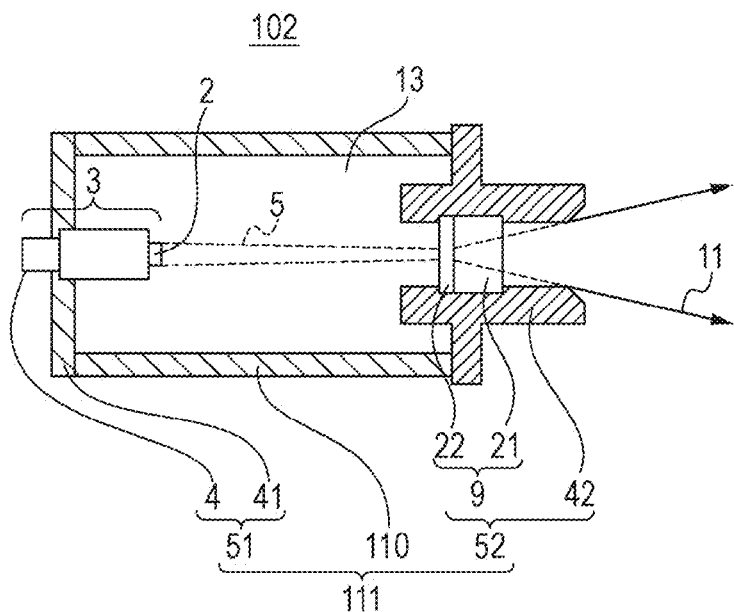
FIG. 5A is a schematic configuration drawing illustrating an X-ray generation tube provided with a transmitting-type target of an embodiment.
Figure 5B:
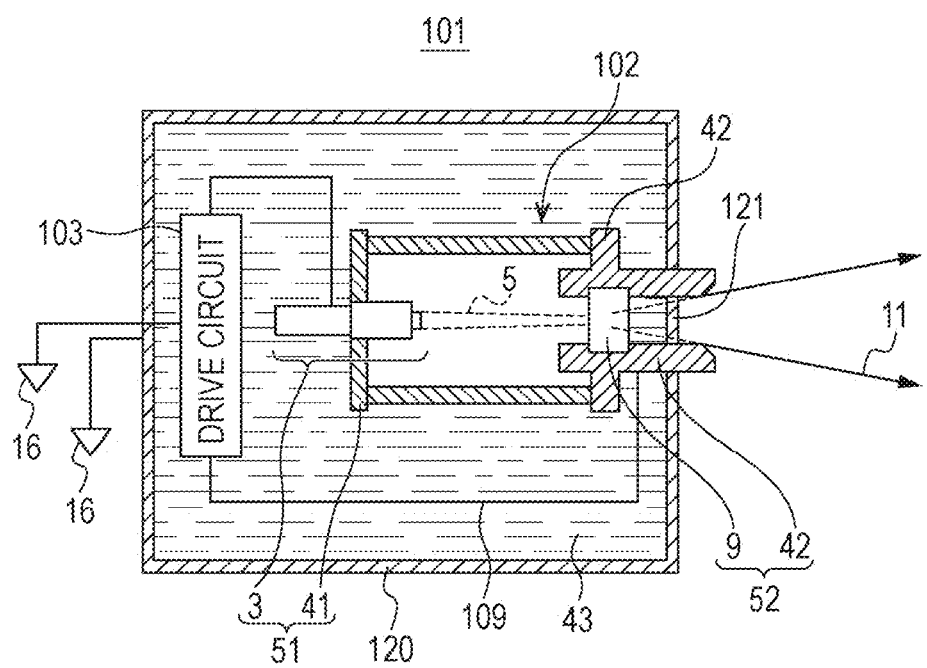
FIG. 5B is a schematic configuration drawing illustrating an X-ray generation apparatus provided with a transmitting-type target of an embodiment.

First of all, an X-ray generation tube and an X-ray generation apparatus to which a transmitting-type target of this disclosure can be applied will be described. FIGS. 5A and 5B are configuration drawings of respective embodiments illustrating an X-ray generation tube 102 and an X-ray generation apparatus 101 provided with a transmitting-type target 9 of this disclosure, respectively.

X-Ray Generation Tube

FIG. 5A illustrates the embodiment of the transmitting-type X-ray generation tube 102 having an electron emitting source 3 and the transmitting-type target 9. Hereinafter, the transmitting-type target 9 is referred to as the target 9 in this specification.

In the first embodiment, a target layer 22 is irradiated with an electron beam 5 emitted from an electron emitting portion 2 provided on the electron emitting source 3, whereby X-ray radiation is generated. Therefore, the target layer 22 is arranged on a transmissive substrate (diamond substrate) 21 on the electron emitting source side, and the electron emitting portion 2 is arranged so as to oppose the target layer 22.

In this embodiment, an X-ray generated in the target layer 22 is limited in emission angle by a collimator having an opening in front of the target 9 as needed as illustrated in FIG. 5A, and is formed into an X-ray beam 11. In this embodiment, a tubular anode member 42 configured to hold the target 9 inside the tube thereof functions as the collimator.

Electrons included in the electron beam 5 are accelerated to an incident energy required for generating the X-ray radiation in the target layer 22 by an accelerating electric field formed in an internal space 13 of the X-ray generation tube 102 interposed between a cathode 51 and an anode 52.

In this embodiment, the anode 52 includes at least the target 9 and the anode member 42, and functions as an electrode that determines an anode potential of the X-ray generation tube 102.

The anode member 42 is formed of a conductive material and is electrically connected to the target layer 22. The anode member 42 of this embodiment is connected to the periphery of the transmissive substrate 21 to hold the target 9 as illustrated in FIG. 5A. The anode member 42 contains heavy metals such as tungsten and tantalum, and functions as the collimator by having a form including an extended portion on the front side of the target 9 with the opening remaining therein as illustrated in FIG. 5A. Detailed embodiments of the target 9 will be described later.

An internal space 13 of the X-ray generation tube 102 is vacuumed for the purpose of securing an average free strokes of the electron beam 5. The degree of vacuum in the interior of the X-ray generation tube 102 is preferably between 1E-8 Pa and 1E-4 Pa inclusive, and more preferably, between 1E-8 Pa and 1E-6 Pa inclusive in terms of the lifetime of the electron emitting source 3. In this embodiment, the electron emitting portion 2 and the target layer 22 are arranged in the internal space 13 or on the inner surface of an enclosure (X-ray generation tube 102), respectively.

The internal space 13 of the X-ray generation tube 102 can be vacuumed by evacuating air therefrom by using an exhaust pipe and a vacuum pump, which are not illustrated, and then sealing the exhaust pipe. In the internal space 13 of the X-ray generation tube 102, a getter, which is not illustrated, may be arranged for the purpose of maintaining the vacuum degree.

The X-ray generation tube 102 includes an insulative tube 110 in a body portion thereof for the purpose of achieving electric insulation between the electron emitting source 3 having a negative potential and the target layer 22 having an anode potential. The insulative tube 110 is formed of an insulative material such as a glass material or a ceramic material. In this embodiment, the insulative tube 110 has a function to define a distance between the electron emitting portion 2 and the target layer 22.

An enclosure 111 is preferably formed of a tough member having hermeticity and atmospheric-pressure-resistant properties for maintaining the vacuum degree. In this embodiment, the enclosure 111 includes the insulative tube 110, the cathode 51 provided with the electron emitting source 3, and the anode 52 provided with the target 9.

Therefore, in this embodiment, the cathode 51 and the anode 52 are connected respectively to both opposed ends of the insulative tube 110, thereby constituting part of the enclosure 111. In the same manner, the transmissive substrate 21 serves as a transmitting window for taking an X-ray generated in the target layer 22 out of the X-ray generation tube 102, and may be said to constitute part of the enclosure 111.

The electron emitting source 3 is provided so as to oppose the target layer 22 provided on the target 9. The electron emitting source 3 may be a hot cathode such as a tungsten filament and an impregnated cathode, or a cold cathode such as a carbon nanotube. The electron emitting source 3 can be provided with a grid electrode and an electrostatic lens electrode, which are not illustrated, for the purpose of controlling a beam diameter of the electron beam 5, an electronic current density, and ON-Off timing.

X-Ray Generation Apparatus

FIG. 5B illustrates the embodiment of the X-ray generation apparatus 101 configured to take the X-ray beam 11 toward the front of an X-ray transmitting window 121. The X-ray generation apparatus 101 of this embodiment includes the X-ray generation tube 102 as an X-ray source and a drive circuit 103 for driving the X-ray generation tube 102 in the interior of a storage container 120 having the X-ray transmitting window 121.

A tube voltage Va is applied between the cathode 51 and the anode 52 by the drive circuit 103, and an accelerated electric field is formed between the target layer 22 and the electron emitting portion 2. By setting the tube voltage Va as needed corresponding to a layer thickness and the type of the metal of the target layer 22, the type of ray required for radiographing may be selected.

The storage container 120 which houses the X-ray generation tube 102 and the drive circuit 103 preferably has a sufficient strength as a container, and is superior in heat dissipation properties, and may be formed of, for example, metallic materials such as brass, iron, stainless steel.

In this embodiment, an insulative liquid 109 is filled in a remaining space 43 in the interior of the storage container 120 other than the X-ray generation tube 102 and the drive circuit 103. The insulative liquid 109 is liquid having insulating property, and has a function for maintaining the electric insulative property in the interior of the storage container 120 and a function as a cooling medium of the X-ray generation tube 102. The insulative liquid 109 used here is preferably insulative oil such as mineral oil, silicone oil, or perfluoro-based oil.

X-Ray Imaging System

Subsequently, a configuration example of an X-ray imaging system 60 provided with the target 9 of this disclosure will be described with reference to FIG. 5C.

A system control unit 202 performs integrated control of the X-ray generation apparatus 101 and an X-ray detector 206. The drive circuit 103 outputs various control signals to the X-ray generation tube 102 under the control of the system control unit 202. The drive circuit 103 is housed in the interior of the storage container 120 of this embodiment provided in the X-ray generation apparatus 101 together with the X-ray generation tube 102. However, the drive circuit 103 may be arranged outside of the storage container 120. An emission state of the X-ray beam 11 emitted from the X-ray generation apparatus 101 is controlled by a control signal output from the drive circuit 103.

The X-ray beam 11 emitted from the X-ray generation apparatus 101 is adjusted in radiation range thereof by a collimator unit, not illustrated, provided with a movable diaphragm, is emitted out of the X-ray generation apparatus 101, is transmitted through a subject 204, and is detected by the detector 206. The detector 206 converts the detected X-ray to an image signal and outputs the image signal to a signal processing unit 205.

The signal processing unit 205 performs a predetermined signal processing on the image signal under the control of the system control unit 202, and outputs the processed image signal to the system control unit 202.

The system control unit 202 outputs a display signal for displaying images on a display device 203 to the display device 203 on the basis of the processed image signal.

The display device 203 displays the image on the basis of the display signal on a screen as a photographed image of the subject 204.

The X-ray imaging system 60 may be used for a non-destructive inspection for industrial products, or for disease diagnosis of human bodies or animals.

Target

Subsequently, embodiments of the target 9 of this disclosure will be described with reference to FIGS. 1A and 1B, FIGS. 2A and 2B, FIGS. 3A and 3B, and FIGS. 4A and 4B.

An embodiment illustrated in FIGS. 1A and 1B and FIGS. 2A and 2B are an embodiment in which the target layer 22 is formed on a surface 24 having a smaller average crystal grain diameter in comparison with a surface 25 opposing thereto, and this embodiment is referred to as the first embodiment of this specification. In contrast, an embodiment illustrated in FIGS. 3A and 3B and FIGS. 4A and 4B are an embodiment in which the target layer 22 is formed on the surface 24 having a larger average crystal grain diameter in comparison with the surface 25 opposing thereto, and this embodiment is referred to as a second embodiment of this specification. Detailed application of the first and second embodiments will be described later.

Figure 1A:
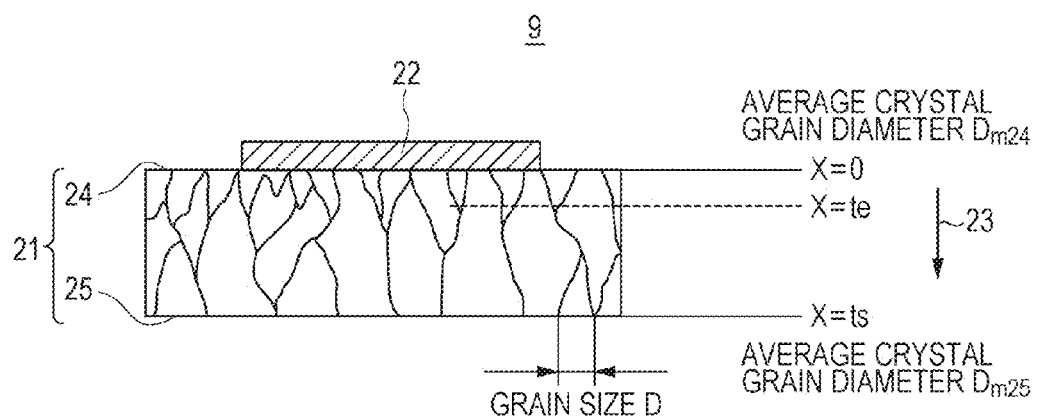
FIG. 1A is a configuration drawing illustrating a transmitting-type target of a first embodiment disclosed here.
Figure 1B:
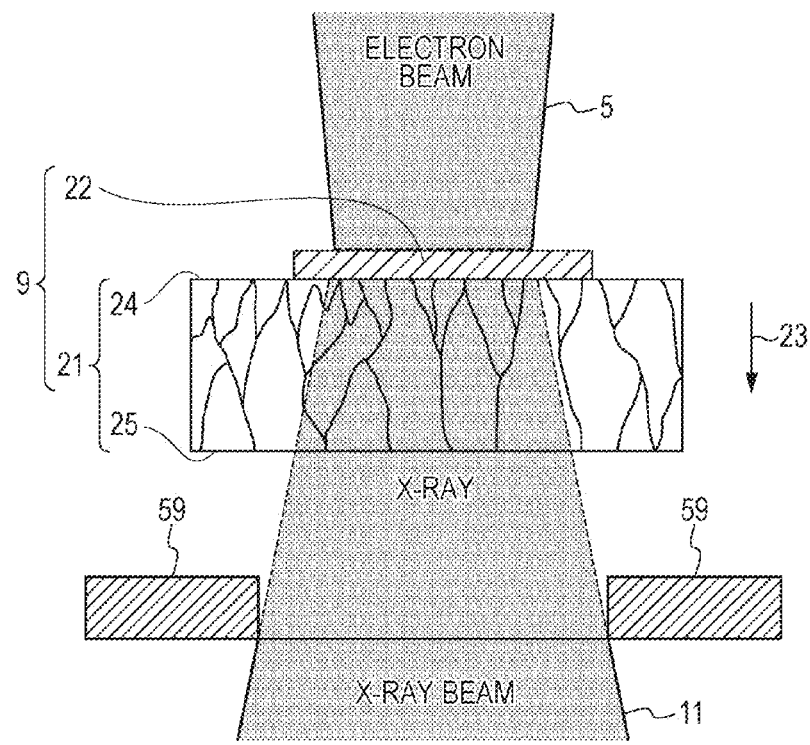
FIG. 1B is a configuration drawing illustrating a transmitting-type target in an operating state thereof.
Figure 3A:
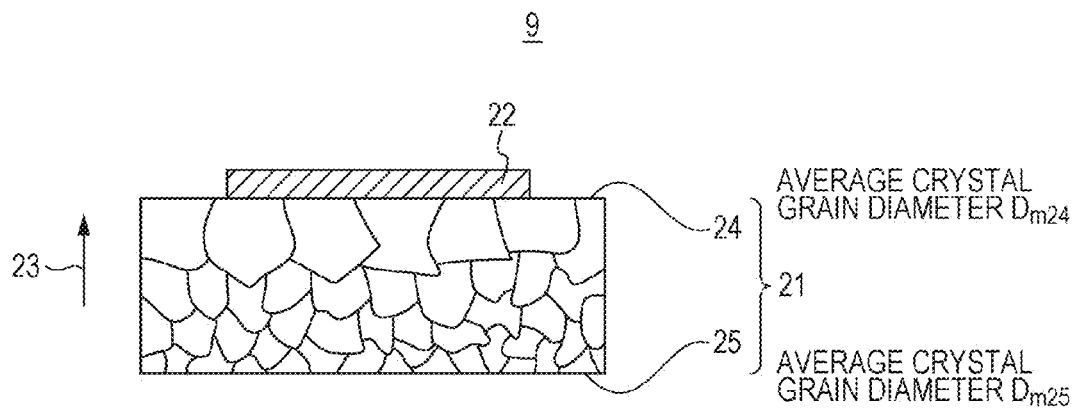
FIG. 3A is a configuration drawing illustrating a transmitting-type target of a second embodiment disclosed here.
Figure 3B:
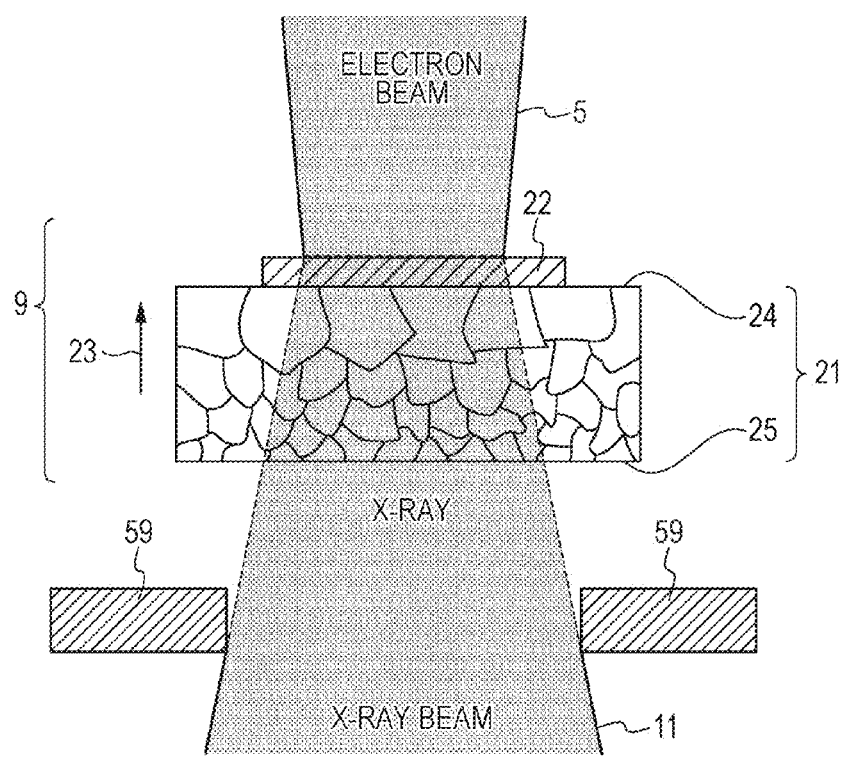
FIG. 3B is a configuration drawing illustrating a transmitting-type target in an operating state thereof.

In the first embodiment and the second embodiment illustrated in FIG. 1A and FIG. 3A respectively, the target 9 includes at least the target layer 22 containing a target metal and the transmissive substrate 21 configured to support the target layer 22. FIG. 1B and FIG. 3B illustrate operating states of the targets 9 illustrated in FIG. 1A and FIG. 3A, respectively. The X-ray radiation is emitted in a radial state by receiving an irradiation of the electron beam 5 by one of the surfaces of the target layer 22.

Part of the X-ray radiation emitted from the target layer 22 of the target 9 of this disclosure transmitted through the transmissive substrate 21 in a substrate thickness direction is formed into the X-ray beam 11 by a collimator 59 having an opening and is taken out to the front of the transmissive substrate 21. In FIG. 1B and FIG. 3B, only an emitted component of the X-ray generated from a focal point of the electron beam radiated on the target layer 22 in a radial state in a range formed by connecting the X-ray beam 11 and the focal point is indicated by broken lines.

The transmissive substrate 21 is formed of polycrystalline diamond having a distribution of the crystal grain diameter in the substrate thickness direction. A chemical vapor-phase deposition method (CVD method), a solid-phase baking method that bakes and solidifies fine crystal diamond, or a liquid-phase baking method that bakes a binder metal such as cobalt and fine crystal diamond by resolution and precipitation action are applied for manufacturing the transmissive substrate 21 formed of the polycrystalline diamond. In terms of beam quality and thermal conductivity of the X-ray, the chemical vapor-phase deposition method is preferably used because elements other than carbon and carbon bonding other than sp3 bonding are small.

The polycrystalline diamond on the basis of the chemical vapor-phase deposition method may be formed into a self-contained polycrystalline diamond layer by forming a film of the polycrystalline diamond on a seed crystal substrate and removing the seed crystal substrate mechanically or chemically.

An outline of the transmissive substrate 21 has a flat panel shape having the one of the pair of surfaces 24 and the other of the pair of surfaces 25 opposing each other as illustrated in FIG. 1A and FIG. 3A, and, for example, a parallelepiped shape or a disk shape is employed.

The disk-shaped transmissive substrate 21 having a diameter of 2 mm to 10 mm is capable of providing the target layer 22 on which a required focal point diameter may be formed, and that having a thickness of 0.3 mm to 3 mm is capable of securing transmissivity of radiation. When a diamond base material having a parallelepiped shape is employed, the range of the diameter described above may be replaced by the lengths of a short side and a long side of a surface of the parallelepiped.

The target layer 22 contains a metallic element having a high atomic number, a high melting point, and a high specific gravity as the target metal. The target metal is preferably at least one type of metal selected from a group of tantalum, molybdenum, and tungsten having a negative standard free energy of formation of carbide in terms of affinity with respect to the transmissive substrate 21. The target metal may be contained in the target layer 22 as a pure metal having a single composition or an alloy composition, or may be contained as a metallic compound such as carbide, nitride, and oxynitride, of the metal.

The layer thickness of the target layer 22 is selected from a range between 1 μm and 12 μm. A lower limit and an upper limit of the layer thickness of the target layer 22 are determined from the view point of securement of an X-ray output intensity and reduction of interface stress, and a range between 3 μm and 9 μm is preferable.

The target 9 includes the anode member 42, a wax material 48, and a conductive electrode 47 in the embodiment illustrated in FIG. 2A and FIG. 4A in order to constitute part of the anode 52 of the X-ray generation tube. The conductive electrode 47 is a conductive member provided in accordance with a necessity for establishing an electric connection with respect to the anode member 42. Examples of the material of the conductive electrode 47 include metals such as tin, silver, and copper, or metallic oxide.

The wax material 48 has a function of holding the target 9 on the anode member 42 and has a function of electric connection between the target layer 22 and the anode member 42. The wax material 48 is an alloy containing gold, silver, copper, tin, and the like, and may ensure the adhesiveness between different materials such as the transmissive base material 21, the conductive electrode 47, and the anode member 42 by selecting an alloy composition depending on the joined member as needed.

The embodiment illustrated in FIG. 2B and FIG. 4B are modifications of the anode 52 illustrated in FIG. 2A and FIG. 4A. In these examples, the transmissive substrate 21 is tapered so that the cross sectional area thereof is reduced in a substrate thickness direction 23 of the transmissive substrate 21 toward the surface 24 that supports the target layer 22.

In the anode 52 illustrated in FIG. 2B and FIG. 4B, angles between side surfaces and the surface 24 is an obtuse angle compared with the anode 52 illustrated in FIG. 2A and FIG. 4A, respectively. Therefore, an effect that stress concentration to a peripheral edge of the surface that supports the target layer 22. The anode 52 of the first embodiment has an effect that protrusion of the wax material 48 toward the front side of the target 9 is restrained when the case where the wax material 48 is protruded occurs. The protrusion of the wax material 48 may be caused when the amount of application of the wax material is uneven or excessive, or when a compression stress is applied to the wax material 48, and the embodiments illustrated in FIG. 2B or FIG. 4B address such problems.

Subsequently, the relation with respect to the transmissive substrate 21 will be described in detail with reference to FIG. 8, FIG. 9, FIG. 11, and FIG. 12.

A disadvantage of conventional technology relates to an operation instability including an electric discharge, the anode current, and X-ray output variation observed in the X-ray generation tube having a transmissive substrate formed of a polycrystalline diamond. The fact that the X-ray generation tube having instability has a co-relation between a crystal grain diameter distribution of the polycrystalline diamond and the surface where the target layer is formed is found as a result of diligent inspection and experimental studies performed by the present inventors.

According to the result of the inspection of conventional diamond-based substrates, performed by the present inventors, it was found that a crack of the transmissive substrate generated on the basis of the distribution of crystal grain fields of the polycrystalline diamond disadvantageously occurs. In addition it was found that separation and missing of the target layer, the connecting electrode, and the wax material due to the crystal grain fields density of the polycrystalline diamond. In particular, in the operating state in which the target is subjected to a thermal shock or mechanical vibrations in association with the pulse drive, a crack of the transmissive substrate is very likely to occur. In addition, in the case where the transmissive substrate has sp2 bonding in the crystal grain fields, separation and missing of the target layer, the connecting electrode, and the wax material is likely to occur.

Figure 9A:
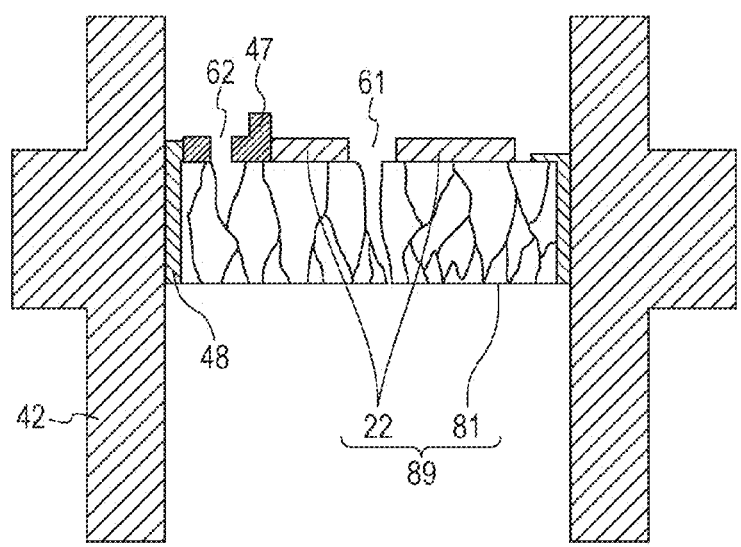
FIG. 9A is an explanatory drawing illustrating conduction failure portions (cracks) 61 and 62 found in an anode 91 of the first reference (comparative) example.

In a first reference example in FIG. 9A illustrates an anode 91 taken out from an X-ray generation tube in which the electric discharge and lowering of the anode current were observed in an endurance acceleration test. The anode 91 included a target 89, the anode member 42, the wax material 48, and the conductive electrode 47, and the target 89 included a transmissive substrate 81 formed of a polycrystalline diamond and a target layer 22.

In the anode 91, minute conduction failure portions 61 and 62 was found in the transmissive substrate 21 as illustrated in FIG. 9A. The conduction failure portion 61 was located in an area of the target layer 22, and part of the target layer 22 and part of a transmissive base material 21 were missing from the target 89. The conduction failure portion 62 was located in an area of the conductive electrode 47, and part of the conductive electrode 47 and part of the transmissive base material 21 were missing from the target 89. As a result of observation of the cross section of the transmissive substrate 81 in the first reference example, the respective observed missing portion was determined to be missed along the crystal grain field.

Figure 9B:
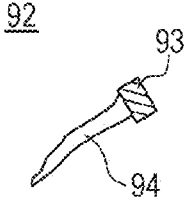
FIG. 9B is an explanatory drawing illustrating a particle substance 92.
Figure 9C:
FIG. 9C is an explanatory drawing illustrating a particle substance 95.

As a result of inspection of the interior of the X-ray generation tube of the first reference example, a particle substance 92 and a particle substance 95 as illustrated in FIGS. 9B and 9C were adhered to an interior of an enclosure. The particle substance 92 included a thin strip 93 formed of a target metal contained in the target layer, and a diamond strip 94 extending from the thin strip 93 in a substantially perpendicular direction. The particle substance 95 included a thin strip 96 formed of a conductive material contained in the conductive electrode 47 and a diamond strip 97 extending from the thin strip 96 in a substantially perpendicular direction. The particle substance 92 and the particle substance 95 were found to be liberated strips of the target 89 corresponding to the conduction failure portions 61 and 62.

In the endurance acceleration test conducted on the X-ray generation tube of the reference example, an anode-grounded X-ray generation tube was prepared, an operating period in which one minute cycles including exposure periods and stop periods are repeated was set to 10 hours, and a load of 0.1 Hz, 0.1N was applied to the anode member of the X-ray generation tube during the operating period.

A detailed mechanism of the electric discharge and lowering of the anode current generated in the X-ray generation tube of the first reference example was not apparent. However, it was supposed that at least particle substances 92, 95 and conduction failure portion 63 caused by minute cracks generated in the anode 91 were involved.

The particle substances 92 and 95 include diamond strips 94 and 97, which are insulative areas respectively, and thin strips 93 and 96, which are conductive areas, connected to the diamond strips 94 and 97. Therefore, in the interior of the X-ray generation tube to which the tube voltage Va is applied, since an electrification charge having the liberated particle substances was not 0, the particle substances 92 and 95 in accordance with the electric field in the interior of the X-ray generation tube and move toward the anode or the cathode. The moved particle substances 92 and 95 were adhered to or hit against and bounced from the surface of the anode or the cathode. It was determined that the adhered particle substances 92 and 95 repeated a series of actions of being charged with positive or negative charge as a result of contact with the anode or the cathode, being moved toward the opposed cathode or the anode, and moving in a direction parallel or antiparallel to the direction of the electric field in the X-ray generation tube.

The behaviors of the particle substances 92 and 95 as described above were determined from a spike-like anode current variation observed anomalously in the X-ray generation tube of the first reference example, and it was also found that the electric discharge occurred by being triggered by the spike-like anode current variation. Although a direct cause that triggers the electric discharge was not apparent, generation of ion gas in association with collision of the particle substances 92 and 95, and electric field concentration occurring with respect to insulative areas and conductive areas of the particle substances, the insulative tube, the anode, and the cathode caused the electric discharge.

As a result of generation of the particle substance 92, the conduction failure portion 61 in the target 89 formed a crack 63 from which the diamond was locally exposed in the interior of the anode 91. The crack 63 was an area where the insulative diamond was exposed, and was negatively charged from a primary electron energy dependency of a secondary electron emission coefficient of the diamond, and the potential was lowered to a level lower than the periphery of the crack 63. The diamond, having a negative electron affinity, performed field electron emission to a member around the crack 63 having an anode potential. Such a local field electron emission seemed to be a cause of the electric discharge.

With a lipophilic property of the diamond, the amount of accumulated polymerized carbon caused by inevitable residual organic gas such as methane was estimated to be relatively larger in the crack 63 present at a position irradiated with the electron beam 5 than the periphery of the crack 63. Consequently, it was estimated that lowering of the anode current occurred in association with generation of gas and ion caused by the polymerized carbon.

As a result of further inspection about the causes of generation of cracks generated in the target 89 of the first reference example, the present inventors determined that the cracks were caused by the inevitable stress generated in the target 89 and the crystal grain diameter distribution in the substrate thickness direction 23. The estimated mechanism of the crack generation will be described with reference to FIGS. 8A and 8B.

Figure 8A:
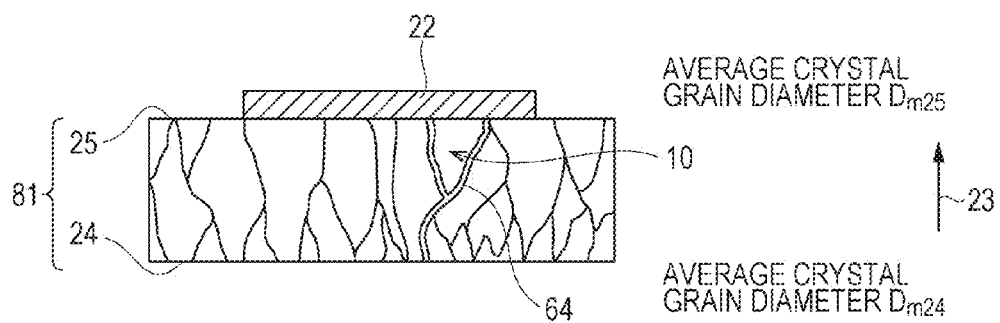
FIG. 8A is an explanatory drawing illustrating a crack development mode of a target 89 of a first reference example.
Figure 9D:
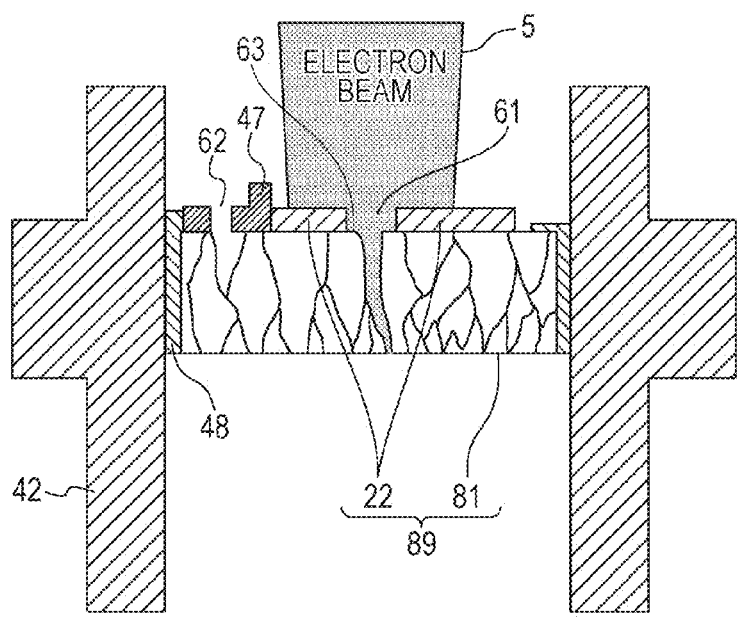
FIG. 9D is an explanatory drawing illustrating an operating state of the comparative example illustrated in FIG. 9A.

FIG. 8A illustrates a development mode of the crack at the time where the target 89 illustrated in FIGS. 9A and 9D. The target 89 of the first reference example had a distribution of the crystal grain diameter in the substrate thickness direction 23 of the transmissive substrate, and had a crystal grain diameter smaller on the surface 25 that supports the target layer than the surface 24 opposed thereto.

A transmissive base member 71 of the target 89 of the first reference example, a crack 64 generated in the substrate thickness direction 23 by a stress generated on the target 89 is illustrated by double line. The crack 64 generated in the transmissive base member 71 of the first reference example was developed along the crystal grain field from the surface 24 to a position immediately beneath the surface 25. An isolated crystal grain 10 was surrounded by the crack 64. The cause of generation of the crack 64 observed in the first reference example, the present inventors reviewed as given below.

It was found from an analysis of a plurality of cracks generated in the transmissive base member 71 of a target 80 of the reference example, it was found that most of the cracks are generated in the crystal grain fields. It is known that the crystal grain fields of the polycrystalline diamond contain impurities and sp2 bonding having a graphite property. Therefore, it was understood that a bonding force is weak in the crystal grain fields, and the cracks can easily be generated.

Therefore, it is understood that the development of the crack differs depending on the crystal grain diameter, and if the crystal grain diameter is relatively small, the development of the crack is impaired and hence the generated crack is small. In contrast, if the crystal grain diameter is large, the length of the generated crack tends to be longer.

Figure 8B:
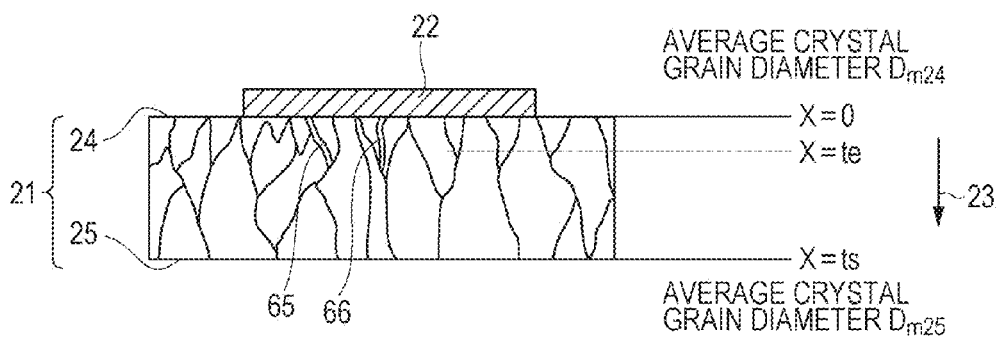
FIG. 8B is an explanatory drawing illustrating a crack development mode of a target 9 of the first embodiment.

Subsequently, anisotropy of the crystal grain fields in the substrate thickness direction 23 and the estimated mechanism which affects the development of the crack will be described with reference to FIGS. 8A and 8B. When the crack was generated on the surface 25 having a larger crystal grain diameter, since the frequency of intersection with other crystal grain fields was low, and hence the development of the crack was not impaired by an intersecting portion, and hence the crack might easily extend to the opposed surface 24 like the crack 64 as illustrated in FIG. 8A. In contrast, when the crack was generated on the surface 24 having a smaller crystal grain diameter, the frequency of intersection with other crystal grain fields was high, and hence the development of the crack was not impaired by the intersecting portion, and stopped in the vicinity of the surface 24 like cracks 65 and 66 illustrated in FIG. 8B.

The review of the present inventors about the stress generated in the transmissive substrate 81 will be described. Stresses such as a thermal stress caused by a thermal shock and a mechanical stress were generated in the transmissive substrate 81. The thermal stress on the basis of the thermal shock was estimated to have generated in the surface 25, which is the surface of the transmissive substrate 81 on the side irradiated with the electron beam caused by a temperature rise at the beginning of irradiation of the electron beam 5 driven in a pulsed manner, for example. As the mechanical stress, a mechanical operation inevitably applied from the outside of the X-ray generation tube or the X-ray generation apparatus applied via a supporting mechanism of the X-ray generation tube or the X-ray generation apparatus was conceivable. The mechanical operation included an adjustment of collimator intended to adjust the exposure field and replacement of filter were included.

Provision of a damper mechanism configured to damper the mechanical stress as described above on the X-ray generation tube or the X-ray generation apparatus was contemplated. However, there was an increase in apparatus weight and secondary vibrations caused by amplitudes of characteristic vibrations of the damper mechanism or the absorbed vibration, and hence complete damping of the mechanical stress was difficult.

Although various types of stress are assumed as the stress generated in the transmissive substrate 81 were supposed, "constrain" of an interface between the target layer 22 and the transmissive substrate 81 and "non-conformity of physical properties" existing on the front and the back might cause the side supporting the target layer to be a starting point of the cracks.

Although not illustrated, a transmissive substrate formed of polycrystalline diamond which does not have asymmetry property in crystal grain diameter distribution in the substrate thickness direction was used, a target layer was formed on either one of the front or back thereof, and the X-ray generation tube integrating the target therein was manufactured. When an operation test of the X-ray generation tube was conducted by applying a weight repeatedly in the same manner as the reference example described above, lowering of the anode current and the electric discharge were observed.

When the X-ray generation tube after having subjected the operation test was disassembled and the target was taken out, the cracks developed to half a thickness of the substrate from the side where the target layer was formed in the substrate thickness direction were observed in the same manner as FIG. 8A.

The cause of the crack was estimated to be because an action of impairing the development of the crack did not occur since the thermal shock generated on the target layer side and the density of the crystal grain fields were not reduced from the surface where the target layer is formed to an opposed surface.

On the basis of the review as described above, the present inventors focused on a process of reduction of the crystal grain fields in the substrate thickness direction of the transmissive substrate, and this disclosure includes the first embodiment characterized in that the target layer is supported on a surface having a smaller crystal grain fields.

With the characteristic of the first embodiment, even though a crack is generated in the transmissive substrate in the case where a stress caused by a thermal shock or a mechanical stress applied from the outside is present, a function of restraining the development of the crack in the substrate thickness direction works, and generation of particle substances liberated from the target may be reduced and occurrence of the electric discharge and lowering of the anode current may be reduced by restraining the development of the crack in the substrate thickness direction.

With the anode 52 provided with the target 9 of the first embodiment illustrated in FIGS. 2A and 2B, generation of the cluck found in the anode 91 of the first reference example is restrained. In the case where the first embodi- ment is applied to the X-ray generation tube, occurrence of the electric discharge and lowering of the anode current with respect to the anode 52 may be reduced.

Figure 12:
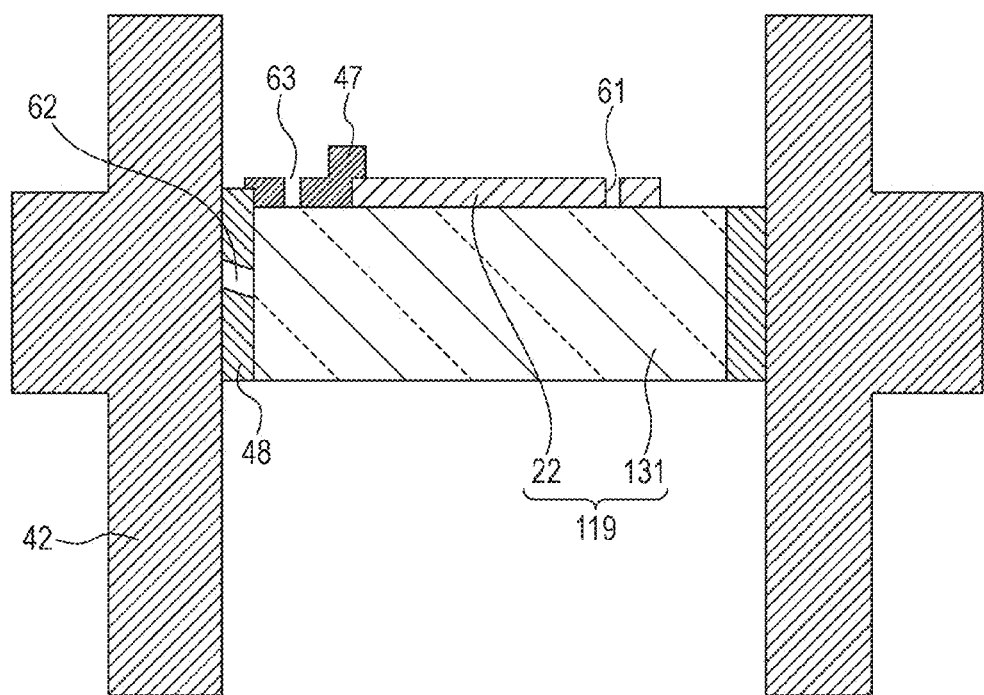
FIG. 12 is an explanatory drawing illustrating cracks 63 found in the anode 141 of the second reference example.

FIG. 12 illustrates an anode 141 in which the X-ray output variation is found after the exposing action has repeated by 1000 times as a second reference example. The anode 141 included a target 119, the anode member 42, the wax material 48, and the conductive electrode 47, and the target 119 included a transmissive substrate 131 formed of a polycrystalline diamond and a target layer 22.

In the anode 141, (a plurality of) minute cracks 61, 62 and 63 were found in each of the target 119 and the wax material 48 respectively as illustrated in FIG. 12. Although the mechanism of the X-ray output variation was not apparent in detail, at least lowering of potential determination performance of the anode caused by minute cracks generated in the anode 141 was involved.

As a result of further inspection about the cracks generated in the anode 141 of the target 119 of the second reference example, the present inventors determined that the cracks were caused by a thermal stress distortion caused by the difference in linear expansion at the time of stopping and at the time of operation. A mechanism of action of the crystal grain diameter distribution of the transmissive base material applied to the potential determination performance of the anode will be described with reference to FIGS. 11A and 11B.

Figure 11A:
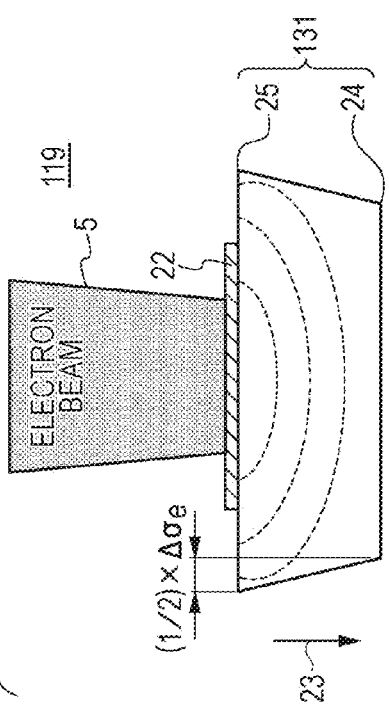
FIG. 11A is an explanatory drawing illustrating a thermal deformation mode and a thermal stress distortion σ of the target 89 of a second reference example.

FIG. 11A illustrates a mode of deformation and an asymmetry property $\Delta\sigma c$ of the thermal stress distortion when the target 119 illustrated in FIG. 12 is in operation. The target 119 had a distribution of the crystal grain diameter in the substrate thickness direction 23 of the transmissive substrate, and had a crystal grain diameter smaller on the surface 25 that supports the target layer than the surface 24 opposed thereto. In the target 119 illustrated in FIG. 11A, the crystal grains and the distributions of the crystal grain fields are omitted. In the target 119, the asymmetry property $\Delta\sigma c$ of the thermal stress distortion in the substrate thickness direction 23 means a difference between the thermal stress distortion $\sigma c_{24}$ of the surface 24 and the thermal stress distortion $\Delta\sigma c_{25}$ of the surface 25.

In the target 119, a state in which the temperature distribution is generated in the substrate thickness direction 23 of the transmissive substrate 21 by heat generation on the surface 25 supports the target layer 22 is indicated by isothermal lines expressed by the broken lines. When the temperature difference between the surface 25 and the surface 24 of the target 119 at the stop period and the operating time were expressed by $\Delta T_{25}$ and $\Delta T_{24}$ respectively, a relationship $\Delta T_{25} > \Delta T_{24}$, was satisfied.

In contrast, the target 119 of the second reference example was estimated to have an asymmetry property of a coefficient of linear expansion a caused by the surface density of the crystal grain fields in the substrate thickness direction 23 of the transmitting substrate. The present inventors reviewed the reason as descried below.

Monocrystal grains and the crystal grain fields which constitute the polycrystalline diamond are difference in composition of a carbon frame structure. The monocrystal grains are governed by sp3 bonding frame structure and has a continuity in the crystal grains. However, the crystal grain field contain the sp2 bonding frame structure by a predetermined concentration.

The target 119 receives a supply of various types of heat in a manufacturing process of being assembled in the X-ray generation tube and at the time of operation generating the X-ray. It is known that the crystal grain fields are liable to be altered from the sp3 bonding to sp2 bonding more than in the crystal grains in the case where the polycrystalline diamond is applied to the transmissive substrate 131. Therefore, the concentration of the sp2 bonding of the crystal grain fields increases before and after heating on a priority basis in comparison with the interior of the crystal grains. In other words, the target having the transmissive substrate having a density distribution of the crystal grain fields can be said to have a higher concentration of the sp2 bonding on the surface where the crystal grain boundary density is high than the surface having a low crystal grain boundary density.

The coefficient of linear expansion of the monocrystal diamond having an ideal sp3 bonding frame structure as a principal component was 1.0 ppm/K at 20° C. In contrast, the coefficient of linear expansion of the monocrystal diamond having a sp2 bonding frame structure as a principal component was 3.1 ppm/K at 20° C. Therefore, the surface 25 having a small crystal grain diameter had a high density of the sp2 bonding and was a surface having a large coefficient of linear expansion a corresponding to the high density of the crystal grain fields. Therefore, a relationship $\alpha_{25} > \alpha_{24}$, where $\alpha_{24}$ and $\alpha_{25}$ were the coefficients of linear expansion of the surface 25 and the surface 24 of the target 119, respectively was established.

The thermal stress distortion σ is proportional to a product of the coefficient of linear expansion a and a temperature difference ΔT, the asymmetry property Δσc of the thermal stress distortion occurring in the substrate thickness direction 23 at the time of operation of the target 119 of the second reference example becomes large by synergetic effect of the asymmetry property of a and the asymmetry property of ΔT with respect to each other as illustrated in FIG. 11A.

In the anode 141, it was estimated that cracks was generated in the target layer 22, the conductive electrode 47, and the wax material 48 because the asymmetry property Δσc of the large thermal stress distortion was generated.

Figure 11B:
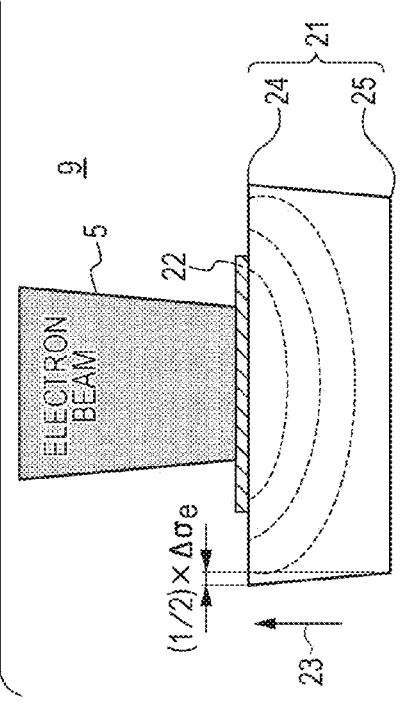
FIG. 11B is an explanatory drawing illustrating a thermal deformation mode and a thermal stress distortion σ of the target 9 of the second embodiment.

FIG. 11B illustrates target 9 according to the second embodiment. FIG. 11B illustrates a mode of deformation and a thermal stress distortion Acre when the target 9 illustrated in FIG. 3A is in operation. In this embodiment of FIG. 11, the surface 24 having a distribution of the crystal grain diameter in the substrate thickness direction 23 of the transmissive substrate 21 and configured to support the target layer 22 had a crystal grain diameter larger than the crystal grain diameter in the other of the pair of surfaces 25 opposing thereto. In the target 9 illustrated in FIG. 11B, the crystal grains and the distribution of the crystal grain fields illustrated in corresponding FIG. 3B are omitted. In the target 119 of this embodiment, the asymmetry property Acre of the thermal stress distortion in the substrate thickness direction 23 means a difference between the thermal stress distortion $\sigma c_{24}$ of the surface 24 and the thermal stress distortion $\Delta \sigma e_{25}$ of the surface 25.

In this embodiment as well, in the same manner as the reference example, a state in which the temperature distribution is generated in the transmissive substrate 21 in the substrate thickness direction 23 by heat generation in the target layer 22 was indicated by isothermal lines expressed by the broken lines. When the temperature difference between the surface 24 and the surface 25 of the target 9 of this embodiment at the stop period and the operating time were expressed by $\Delta T_{24}$ and $\Delta T_H$ respectively, a relationship $\Delta T_{24} > \Delta T_H$, was satisfied.

Also, the surface 24 having a large crystal grain diameter had a low concentration of the sp2 bonding and was a surface having a small coefficient of linear expansion a corresponding to the low density of the crystal grain fields. Therefore, a relationship $\alpha_{24} > \alpha_{25}$, where $\alpha_{24}$ and $\alpha_{25}$ were coefficients of linear expansion of the surface 24 and the surface 25 of the target 9 of this embodiment, respectively, was established.

The thermal stress distortion σ is proportional to a product of the coefficient of linear expansion a and a temperature difference ΔT, the asymmetry property Δσe of the thermal stress distortion occurring in the substrate thickness direction 23 at the time of operation of the target 9 of this embodiment becomes small by canceling effect of the asymmetry property of α and the asymmetry property of ΔT as illustrated in FIG. 11B. In this manner, in the target 9 of the second embodiment, it can be said that a mechanism that a distribution of coefficient of linear expansion in the substrate thickness direction caused by the crystal grain boundary density cancels out a distribution of calorific power in the substrate thickness direction caused by incident electron beam works.

Although not illustrated, a transmissive substrate formed of polycrystalline diamond which does not have asymmetry property in crystal grain diameter distribution in the substrate thickness direction was used to heat the transmissive substrate under a reduced atmosphere. A target layer was formed on either one of front or back of the transmissive substrate, and an X-ray generation tube including the target integrated therein was manufactured. When an operation test of the X-ray generation tube was conducted repeatedly in the same manner as the reference example described above, variations in the X-ray intensity were observed.

When the X-ray generation tube subjected to the operation test was disassembled and taken out, a film separation was observed between the target layer and the connection electrode in the same manner as FIG. 12.

The cause of the film separation was estimated that the mechanism of reducing the distribution of the calorific power existing in the substrate thickness direction by the incident electron beam did not work because the crystal grain boundary density has no asymmetry property in the substrate thickness direction.

The concentration of the sp2 bonding in the carbon composition containing diamond may be determined by an electron energy-loss spectroscopy (EELS method) or the like. The concentration of the sp2 bonding may be specified as [sp2 bonding detected concentration]/([sp2 bonding detected concentration]+[sp3 bonding detected concentration]).

With the anode 52 provided with the target 9 of this embodiment illustrated in FIGS. 4A and 4B, generation of the crack found in the anode 141 of the reference example is restrained. In the case where the first embodiment is applied to the X-ray generation tube, lowering of the potential determination performance with respect to the anode 51 and the output variation of the X-ray may be reduced.

As the transmissive substrate 21 having a crystal grain diameter distribution in the substrate thickness direction 23 as illustrated in FIG. 1A and FIG. 3A, a self-contained polycrystalline diamond formed by the chemical vapor-phase deposition method may be applied.

In the self-contained polycrystalline diamond formed by the chemical vapor-phase deposition method is obtained by causing crystal growth of the polycrystalline diamond from a plasma atmosphere on the seed crystal substrate, which is not illustrated, and then removing the seed crystal substrate.

The crystal grain diameter distribution in the substrate thickness direction 23 of the transmissive substrate 21 obtained by the chemical vapor-phase deposition method may be controlled by selecting a condition of film formation and a condition of seed crystal.

Figure 6A:
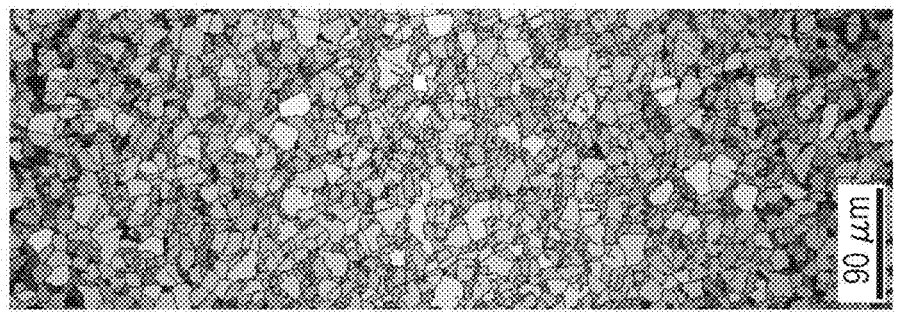
FIG. 6A illustrates an image of a surface 24 of the transmissive substrate of the transmitting-type target of the first embodiment, the image was observed by an electron backscattering diffraction method.
Figure 6B:
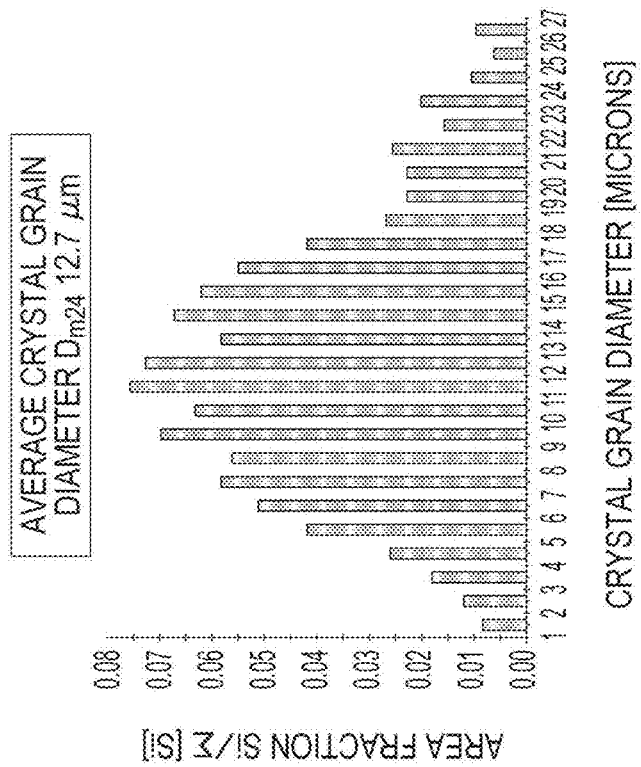
FIG. 6B illustrates a crystal grain diameter distribution of the surface 24.
Figure 6D:
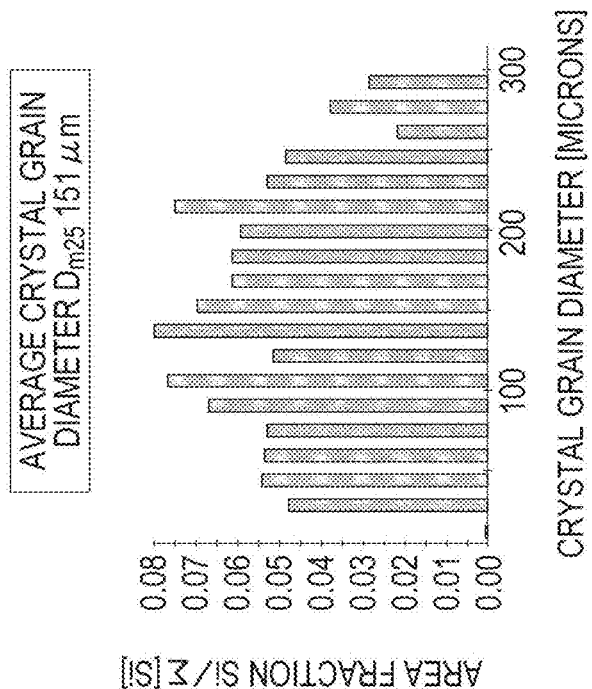
FIG. 6D illustrates a crystal grain diameter distribution of the surface 25.
Figure 6C:
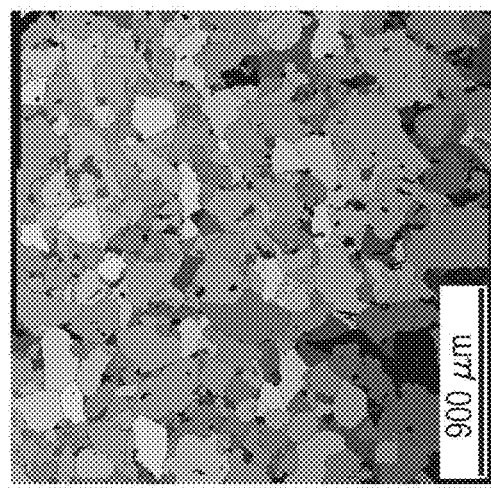
FIG. 6C illustrates an image of the surface 25 of the transmissive substrate of the transmitting-type target of the first embodiment, the image was observed by the electron backscattering diffraction method.

FIGS. 6A and 6C are polycrystalline images of the surface 24 and the surface 25 of the transmissive substrate 21 obtained by the chemical vapor-phase deposition method observed by an electron backscattering diffraction method (EBSD method). The areas where the condensation is uniform in the respective observed images are a monocrystal domain having the crystal aligned orientation, which corresponds to the crystal grains of this disclosure. The boundaries between the respective monocrystal domains correspond to the crystal grain fields of this disclosure.

In a polycrystalline material formed by the chemical vapor-phase deposition method, the crystal grain diameter on the seed crystal substrate side is limited to the size corresponds to the growth nucleus of the seed crystal substrate. When the polycrystalline diamond is formed by the chemical vapor-phase deposition method, the crystal grains of the monocrystal diamond grows in the direction perpendicular to the substrate thickness direction 23 from a plurality of growth nucleus. In the process of the crystal growth in the direction perpendicular to the substrate thickness direction 23, crystal grains which grow relatively larger from any cause are generated.

If there arises the case where a certain crystal grain become dominant and other crystal grains adjacent thereto disappear due to the difference in growing speed between the adjacent crystal grains, it is considered that increase in average crystal grain diameter and decrease in surface density of a crystal interface occur in the substrate thickness direction 23.

Such a crystal growth process may be considered as the growth of the crystal interface in the substrate thickness direction 23. When the crystal interface which defines a certain crystal grain grows in the substrate thickness direction 23, there arise a stage in which the crystal grain intersects with other crystal grain fields adjacent thereto and one of the crystal interfaces disappears. This state corresponds to a disappearing stage in the process of crystal growth of one of the crystal grains in the substrate thickness direction 23.

In the first embodiment, the transmissive substrate 21 includes column-shaped crystal grains extending in the substrate thickness direction 23 existing therein illustrated in FIG. 1A, and the crystal grain fields which are present between the crystal grains have a component extending in the substrate thickness direction. Such a crystal component is controlled by a building-up condition as described later. The transmissive substrate 21 having the crystal grains and the crystal grain fields extending in the substrate thickness direction is superior in heat dissipating properties in the substrate thickness direction. On the other hand, as described above, the development of the crack along the crystal grain field may cause thermal shock or a mechanical stress which is not desirable.

In FIG. 1A, the case where an average distance from the surface of the seed crystal substrate to a stage where the crystal interface disappears is expressed by te, the position of the seed crystal substrate (the surface 24) is expressed by x=0, and the position of the growing surface (the surface 25) is expressed by x=ts will be considered. "x" is an actual number between 0 and is inclusive.

An average line density of the crystal grains at a position x of the substrate thickness direction 23 of the transmissive substrate 21 is reduced by (x/te) power of (½) with respect to the average line density of the crystal grain on the seed crystal substrate side. In other words, the average crystal grain diameter in the position x of the substrate thickness direction 23 of the transmissive substrate 21 is increased by (x/te) power of 2 with respect to the seed crystal substrate side.

Therefore, an average line density of the crystal grains of the surface 25 on the growing surface side with respect to the surface 24 on the seed crystal substrate side is reduced by (ts/te) power of (½) with respect to the average line density of the crystal grains on the seed crystal substrate side. In other words, the average crystal grain diameter of the surface 25 with respect to the surface 24 is a value increased to (ts/te) power of 2.

As described above, in the case where the precursor of the target 9 is built up on the seed crystal substrate by the chemical vapor-phase deposition method, if the precursor is built up so that the average crystal grain diameter increases in the building up direction, the target 9 of the first embodiment can be formed by using the seed crystal substrate side as the surface 24.

In the same manner, in the case where the precursor of the target 9 is built up on the seed crystal substrate by the chemical vapor-phase deposition method, if the precursor is built up so that the average crystal grain diameter increases in the building up direction, the target 9 of the second embodiment can be formed by using the crystal growing surface side as the surface 24.

In contrast, in the case where the precursor of the target 9 is built up on the seed crystal substrate by the chemical vapor-phase deposition method, if the precursor is built up so that the average crystal grain diameter decreases in the building up direction, the target 9 of the first embodiment can be formed by using the crystal growing surface side as the surface 24.

In addition, in the case where the precursor of the target 9 is built up on the seed crystal substrate by the chemical vapor-phase deposition method, if the precursor is built up so that the average crystal grain diameter increases in the building up direction, the target 9 of the second embodiment can be formed by using the seed crystal substrate side as the surface 24.

In the case where a sinter having an isotropic crystal grain diameter distribution is formed, polycrystalline diamond sheets having grain diameters of microcrystal diamond as a material different from each other are built up and sintered, so that the crystal grain diameter distribution may be formed in the building up direction of the polycrystalline diamond sheets.

The electron backscattering diffraction method utilizes the fact that the electron beam irradiated on a specimen formed of a crystalline material and backscattered from the specimen presents an EBSD pattern, and the fact that the EBSD pattern includes information on a crystal shape and a crystal orientation. The EBSD pattern is also referred to as a Kikuchi Line Diffraction Pattern. Furthermore, in the electron backscattering diffraction method, in combination with a scanning electron microscope (SEM), the specimen is scanned by irradiating with an electron beam, and the EBSD pattern is measured and analyzed, whereby information relating to the crystal shape and the crystal orientation in the minute area is obtained.

In this disclosure, in the focused surfaces 24 and 25, a circle having a diameter D which matches the independent monocrystal domain in surface area is assumed to define a crystal grain diameter D. In addition, the crystal grain diameter D of the polycrystalline diamond has the crystal grain diameter distribution as illustrated in FIGS. 6B and 6D, the surface area of the crystal grain and the crystal grain diameter D may be determined by extracting the monocrystal domain by image processing included in the observed polycrystalline image.

Considering the crystal grain diameter distribution of the above-described polycrystalline diamond, in the specification of this disclosure, the surface 25 opposing the surface 24 configured to support the target layer is discriminated and selected by using a magnitude relationship of an average crystal grain diameter Dm considering a surface integral fraction $S_i/\Sigma S_i$. In the specification of this disclosure, the average crystal grain diameter Dm is determined by the following expression when the crystal grain diameter distribution is sampled by the number n of samples in a crystal grain diameter axis in the surface of the transmissive substrate 21 being focused on.

$$D_m = \frac{\sum_{i=1}^{n}(D_i S_i)}{\sum_{i=1}^{n}(S_i)} \quad \text{Expression 1}$$

where, a parameter in the expression given above, a crystal grain diameter larger than a crystal grain diameter and not larger than $D_i$ is $D_i$, a cumulated surface area larger than the crystal grain diameter $D_{i-1}$ and not larger than $D_i$ is $S_i$, i is an integer from 1 to n, and a crystal grain diameter $D_0$ is an actual number not smaller than 0.

The crystal grain diameter distributions illustrated in FIGS. 6B and 6D show the crystal grain diameter (μm) by a lateral axis, and the surface integral fraction $S_i/\Sigma(S_i)$ by a vertical axis. In the sampling on the crystal grain diameter axis, the sampling segment may be a non-equal segment having segment lengths different from each other, or may be the segment of the crystal grain diameter between or larger and smaller than $D_i$.

In order to ensure an averaging accuracy of the crystal grain diameter D, the size of an observation field of view is preferably set as needed in accordance with the sample so that 100 or more monocrystal domains are included in the observation field of view. Considering the crystal grain diameter and the crystal grain diameter distribution included in the observation field of view of the surface 24 and the surface 25, the size of the observation field of view may be changed from one observing surface to another as illustrated in FIGS. 6A and 6D.

In the first embodiment, the surface 24 is a surface of the self-contained polycrystalline diamond on the seed crystal substrate side in the chemical vapor-phase deposition method, and the surface 25 indicates the surface on the growing surface side.

The first embodiment is characterized in that the transmissive substrate 21 has an asymmetry property so that an average density of the crystal grain fields is reduced from the surface 24 configured to support the target layer 22 to the surface 25 opposing thereto in terms of restraint of the development of the crack in the substrate thickness direction 23 of the transmissive substrate 21. In other words, the first embodiment is characterized in that the transmissive substrate 21 has an asymmetry property so that the surface 24 configured to support the target layer 22 has an average crystal grain diameter smaller than that of the surface 25 opposing thereto in terms of restraint of the development of the crack in the substrate thickness direction 23 of the transmissive substrate 21.

Therefore, the ratio of an average crystal grain diameter $D_{m24}$ of the surface 24 configured to support the target layer 22 with respect to an crystal grain diameter $D_{m25}$ of the surface 25 opposing thereto is preferably smaller than 1. The ratio of the average crystal grain diameter $D_{m24}/D_{m25}$ is preferably 0.5 or smaller, and more preferably, 0.2 or smaller.

In order not to allow part of the target layer 22 from being separated by the cracks 65 and 66 inevitably generated on the side of the surface 24 configured to support the target layer 22, the average crystal grain diameter of the surface 24 does not exceeds preferably 10 times the layer thickness of the target layer 22. From the same point of view, the average grain diameter of the surface 24 is further preferably 5 μm and higher and 50 μm or smaller.

In order to limit the development of the cracks 65 and 66 generated inevitably in the surface 25 on the side opposing the surface 24 configured to support the target layer 22, the average crystal grain diameter of the surface 25 is preferably 100 μm or larger.

The second embodiment is characterized in that the crystal grain diameter distribution has an asymmetry property so as to compensate the asymmetry property of the temperature distribution in the substrate thickness direction 23 caused by heat generation of the target layer 22 in terms of alleviation of the asymmetry property of the thermal stress distortion in the substrate thickness direction 23.

Therefore, the ratio of the average crystal grain diameter $D_{m24}$ of the surface 24 configured to support the target layer 22 with respect to the average crystal grain diameter $D_{m25}$ of the surface 25 opposing thereto is preferably larger than 1. The ratio of the average crystal grain diameter $D_{m24}/D_{m25}$ is preferably 1.3 or larger, and more preferably, 5 or larger.

Control of the distribution of the average crystal grain diameter in the substrate thickness direction 23 of the transmissive substrate 21 can be performed in the manner described below. As described above, the average crystal grain diameter of the surface 25 with respect to the surface 24 is a value increased to (ts/te) power of 2. Therefore, control of the distribution of the average crystal grain diameter in the substrate thickness direction 23 of the transmissive substrate 21 is achieved by selecting a thickness ts of the transmissive substrate 21 and an average distance te to a state where the crystal interface disappears from the seed crystal substrate as needed.

The thickness ts of the transmissive substrate 21 is selected as needed from an absorption damping of a radiation generated in the target layer 22 in the substrate thickness direction 23 and a thermal resistance design with respect to the calorific power generated in the target layer 22.

In contrast, the average distance te depends on the condition of building up of the chemical vapor-phase deposition method, and if the building up speed is lowered, the average distance te is increased by an eptaxial growth and, in contrast, if the building up speed is increased, the average distance te is reduced.

In the transmissive substrate 21 illustrated in FIG. 1A, te is 560 μm and ts=2000 μm, so that the average line density of the crystal grain fields of the surface 25 is reduced to approximately 1/11.9 times the surface 24, and the average crystal grain diameter of the surface 25 is increased to approximately 11.9 times the surface 24.

The method of determining the crystal grain diameter distribution is not limited to the electron backscattering diffraction method described above, and the following methods (1) to (4) may be applied.

Minute depressions and projections existing between the crystal grains were observed by a secondary electron image with (1) Nomarski microscope and (2) scanning electron microscope (SEM). (3) The fact that a light-emitting intensity is low in the vicinity of a microscopic cathode luminescence image the crystal grain field is utilized to detect crystal grains. (4) A slice specimen processed by a focused ion beam (FIB) in parallel to the observation surface is prepared, the crystal grains are emphasized in a ring-shaped bright-field image by a scanning type transmissive electronic microscope (TEM), and are specified from an image contrast.

First Exemplary Embodiment

Subsequently, an X-ray generation apparatus provided with the target of this disclosure is created in a procedure given below, and the X-ray generation apparatus is operated to evaluate discharge resistance and stability of the anode current.

The configuration of the target 9 created in this exemplary embodiment is illustrated in FIG. 1A.

As the target 9 of this exemplary embodiment, self-contained polycrystalline diamond created by the chemical vapor-phase deposition method and having a diameter of 5 mm and a thickness of 1 mm was prepared at first. The self-contained polycrystalline diamond was washed to clean a residual organic substance on the surface thereof with an UV ozone washer apparatus to achieve the transmissive substrate 21.

Images of the one of the pair of surfaces 24 of the transmissive substrate 21 used in this exemplary embodiment and the other of the pair of surfaces 25 opposing thereto observed by the electron backscattering diffraction method are illustrated in FIGS. 6A and 6C, respectively. The crystal grain diameter $D_{m24}$ of the one of the pair of surfaces 24 of the transmissive substrate 21 used in this exemplary embodiment was 12.7 μm, and the average crystal grain diameter $D_{m25}$ of the other of the pair of surfaces 25 was 151 μm.

Subsequently, argon gas was used as carrier gas for the surface 24 of the transmissive substrate 21, and a sintered member of tungsten was used as a spatter target, so that a metal-contained layer including tungsten was formed so as to have a thickness of 6 μm by spattering to obtain a laminated member.

The obtained laminated member was sintered in a vacuum image furnace to create the target 9 provided with the target layer 22 formed of tungsten carbide. The layer thickness of the target layer 22 was 7 μm.

The target layer 22 of the target 9 of this exemplary embodiment was formed on the surface 24 which was smaller in average crystal grain diameter Dm than the surface 25 opposed thereto.

Subsequently, the conductive electrode 47 was formed in an area between a peripheral edge of the target layer 22 and a side surface of the transmissive substrate 21, and the wax material 48 formed of a tin-silver alloy was arranged on the side surface of the transmissive substrate 21. Furthermore, the target 9 provided with the wax material 48 and the conductive electrode 47 was arranged in the tube of the tubular anode member 42, and then was heated to create the anode 52 illustrated in FIG. 2A.

Furthermore, the X-ray generation tube 102 illustrated in FIG. 5A was manufactured by using the anode 52 of this exemplary embodiment. When the static pressure resistance of the X-ray generation tube 102 was tested, the tube voltage of 150 kV could be maintained with no discharge continuously for 10 minutes. The static pressure resistance test in this exemplary embodiment was a test for evaluating the discharge voltage resistance by applying a tube voltage between the anode 52 and the cathode 51 without generating an electron beam from the electron emitting source 3 of the X-ray generation tube 102.

Subsequently, the drive circuit 103 was electrically connected to the cathode and the anode of the X-ray generation tube 102, then, the X-ray generation tube 102 and the drive circuit 103 are stored in the interior 43 of the storage container 120, whereby the X-ray generation apparatus 101 illustrated in FIG. 5B was manufactured.

Subsequently, in order to evaluate the discharge-resistant performance and the stability of the anode current of the X-ray generation apparatus 101, an evaluation system 70 illustrated in FIG. 7 was prepared. The evaluation system 70 included a dosemeter 26 arranged at a position 1m in front of the X-ray emitting window 121 of the X-ray generation apparatus 101. The dosemeter 26 was configured to be capable of measuring a radiation output intensity of the X-ray generation apparatus 101 by being connected to the drive circuit 103 via the measurement control unit 203.

A driving condition with respect to the X-ray generation apparatus 101 of this exemplary embodiment was +110 kV as the tube voltage of the X-ray generation apparatus 101, 20 mA/mm as a current density of the electron beam that the target layer 22 is to be irradiated with, and a pulse driving in which 3 seconds of an electron irradiating period and 57 seconds of a non-irradiating period are repeated alternately. The detected anode current was measured by measuring a tube current flowing from the target layer 22 to a grounding electrode 16 as the anode current, and an average value during one second at a center of the electron irradiation pulse width was employed. A rise time and a fall time of the electron irradiation pulse were both set to 0.1 seconds.

A stability evaluation of the anode current was performed by a retention rate retained by standardizing the anode current after 10 hours elapsed from the start of X-ray output by an initial anode current. The X-ray generation tube 102 of this exemplary embodiment was grounded at the anode, and a load of 0.1 Hz, 0.1 N were applied to the anode member 42 of the X-ray generation tube 102 during the operation period.

At the time of the stability evaluation of the anode current, a gate current flowing between the cathode electrode (electron emitting portion 2) and a gate electrode was stabilized so that the variation falls within 1% by a negative feedback circuit, which is not illustrated.

In the test on the discharge resistance, stable driving without electric discharge was confirmed by a discharge counter 76 during the stability evaluation of the anode current of the X-ray generation apparatus 101.

The retention rate of the anode current of the X-ray generation apparatus 101 of this exemplary embodiment was 0.99. It was confirmed that no noticeable variation of the X-ray output was found in the X-ray generation apparatus 101 provided with the target 9 of this exemplary embodiment even after a long term driving history and the stable X-ray output intensity was obtained. When the X-ray generation apparatus 101 after the evaluation of the stability of the anode current was disassembled and the anode 52 was taken out, no crack was found in the target layer 22.

In addition, when the cross section of the taken-out transmissive substrate 21 was observed, no crack was found even though the column-shaped crystal grains extending from the one of the pair of surfaces 24 to the other of the pair of surfaces 25 exist.

Second Exemplary Embodiment

In this exemplary embodiment, an X-ray imaging system 60 illustrated in FIG. 5C was created by using the X-ray generation apparatus 101 described in the first exemplary embodiment. In the same manner as the first exemplary embodiment, a load of 0.1 Hz, 0.1 N was applied to the anode member 42 protruded from the storage container 120 the X-ray generation apparatus 101 to perform X-ray radiographing, whereby a transmitted X-ray image was obtained.

The X-ray generation apparatus 101 in which the target 9 was not damaged by cracks, electric discharge was restrained, and variations in anode current were reduced without damage on the target by cracks even in the case where vibrations were applied to the X-ray generation apparatus 101 was achieved. Therefore, the X-ray imaging system 60 of this exemplary embodiment could obtain an X-ray image having a high SN ratio.

Third Exemplary Embodiment

Subsequently, an X-ray generation apparatus provided with the target of this disclosure is manufactured in a procedure given below, and the X-ray generation apparatus is operated to evaluate output stability.

The configuration of the target 9 created in this exemplary embodiment is illustrated in FIG. 3A.

As the target 9 of the exemplary embodiment, a self-contained polycrystalline diamond created by the chemical vapor-phase deposition method and having a diameter of 5 mm and a thickness of 1 mm was prepared. The self-contained polycrystalline diamond was washed to clean a residual organic substance on the surface thereof with an UV ozone washer apparatus.

Subsequently, a heating process was performed on the self-contained polycrystalline diamond for 60 minutes at 1000° C. under a decompressed atmosphere of a total pressure of 1.1E-6 Pa, and a hydrogen partial pressure of 1E-6 Pa to obtain the transmissive substrate 21. The hydrogen is reducing gas introduced for restraining unnecessary oxidization other than the change in crystal structure of the polycrystalline diamond during the heating process.

Figure 10B:
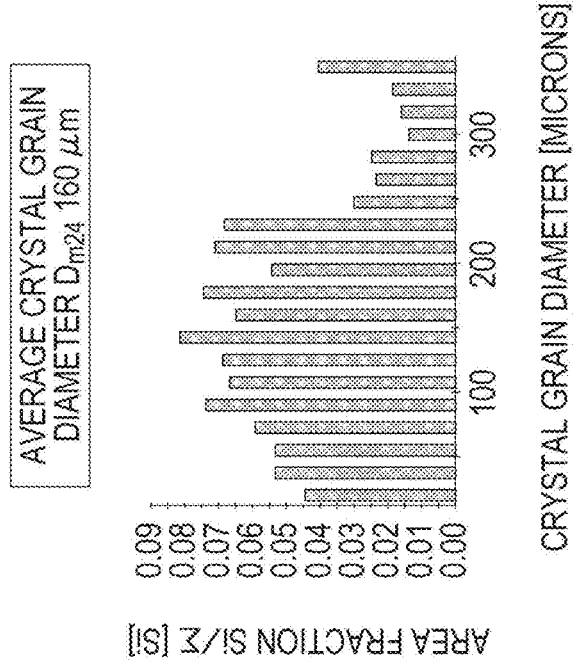
FIG. 10B illustrates a crystal grain diameter distribution of the surface 24.
Figure 10A:
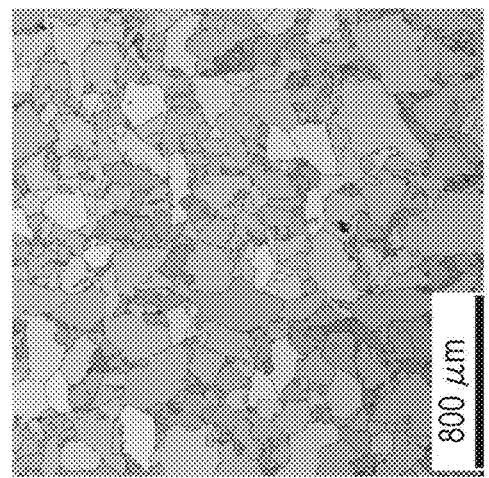
FIG. 10A illustrates an observed image of the surface 24 of the transmissive substrate of the transmitting-type target of the second embodiment by the electron backscattering diffraction method.
Figure 10D:
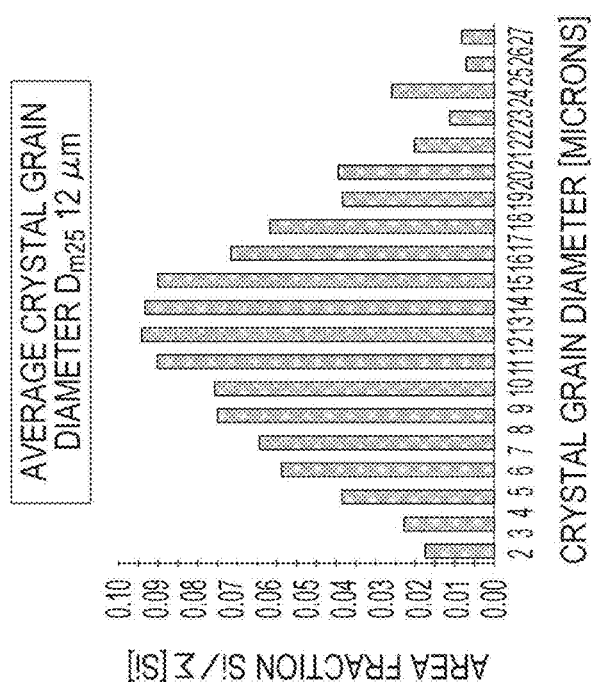
FIG. 10D illustrates a crystal grain diameter distribution of the surface 25.
Figure 10C:
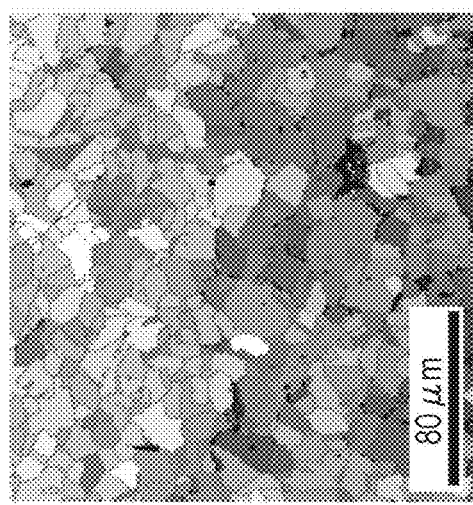
FIG. 10C illustrates an observed image of the surface 25 by the electron backscattering diffraction method.

Images of the surface 24 of the transmissive substrate 21 used in this exemplary embodiment and the surface 25 opposing thereto observed by the electron backscattering diffraction method are illustrated in FIGS. 10A and 10C. The crystal grain diameter $D_{m24}$ of the surface 24 of the transmissive substrate 21 used in this exemplary embodiment was 160 μm, and the average crystal grain diameter $D_{m25}$ of the surface 25 was 12 μm.

Subsequently, when a Raman spectrometry was performed on the transmissive substrate 21, and a Raman shift peak was observed by the number of waves of 1580 $cm^{-1}$ specific for the sp2 bonding, any significant peak was not observed in the crystal grains, but a Raman shift peak having a half bandwidth of 123 $cm^{-1}$ as was observed in the crystal grain fields. Consequently, the transmissive substrate 21 of this exemplary embodiment was confirmed to be a substrate having the sp2 bonding selectively in the crystal grain fields. In the self-contained polycrystalline diamond which was not subjected to the heating process under the above-described reduced gas atmosphere, a significant peak was observed neither within the crystal grains nor the crystal grain fields.

Subsequently, argon gas was used as carrier gas for the surface 24 of the transmissive substrate 21, and a sintered member of a tungsten was used as a spatter target, so that a metal-contained layer including tungsten was formed to have a thickness of 6 μm by spattering to obtain a laminated member.

The obtained laminated member was sintered in a vacuum image furnace to create the target 9 formed of tungsten carbide. The layer thickness of the target layer 22 was 7 μm.

The target layer 22 of the target 9 of this exemplary embodiment was formed on the surface 24 which was larger in average crystal grain diameter Dm than the surface 25 opposed thereto.

Subsequently, the conductive electrode 47 was formed in an area between the peripheral edge of the target layer 22 and the side surface of the transmissive substrate 21, and the wax material 48 formed of a tin-silver alloy was arranged on the side surface of the transmissive substrate 21. Furthermore, the target 9 provided with the wax material 48 and the conductive electrode 47 was arranged in the tube of the anode member 42, and then was heated to create the anode 52 illustrated in FIG. 4A.

Furthermore, the X-ray generation tube 102 illustrated in FIG. 5A was manufactured by using the anode 52 of this exemplary embodiment. When the static pressure resistance of the X-ray generation tube 102 was tested, the tube voltage 150 kV could be maintained with no discharge continuously for 10 minutes. The static pressure resistance test in this exemplary embodiment was a test for evaluating the discharge voltage resistance by applying a tube voltage between the anode 52 and the cathode 51 without generating an electron beam from the electron emitting source 3 of the X-ray generation tube 102.

Subsequently, the drive circuit 103 was electrically connected to the cathode and the anode of the X-ray generation tube 102, then, the X-ray generation tube 102 and the drive circuit 103 are stored in the interior 43 of the storage container 120, whereby the X-ray generation apparatus 101 illustrated in FIG. 5B was manufactured.

Subsequently, in order to evaluate the driving stability of the X-ray generation apparatus 101, an evaluation system 70 illustrated in FIG. 7 was prepared. The evaluation system 70 included a dosemeter 26 arranged at a position 1m in front of the X-ray emitting window 121 of the X-ray generation apparatus 101. The dosemeter 26 is configured to be capable of measuring a radiation output intensity of the X-ray generation apparatus 101 by being connected to the drive circuit 103 via the measurement control unit 203.

A driving condition in evaluation of the driving stability was +110 kV as the tube voltage of the X-ray generation tube 102, 25 mA/mm as a current density of the electron beam that the target layer 22 is to be irradiated with, and a pulse driving in which 1 second of an electron irradiating period and 59 seconds of a non-irradiating period are repeated alternately. An average value for 1 second at a center in the electron irradiation time was employed as the detected X-ray output intensity.

A stability evaluation of the X-ray output intensity was performed by a retention rate evaluated by standardizing the X-ray output intensity after 100 hours elapsed from the start of X-ray output by an initial X-ray output intensity.

At the time of the stability evaluation of the X-ray output intensity, the tube current flowing from the target layer 22 to the grounding electrode 16 was measured, and constant current control is performed to control an electron current irradiated on the target layer 22 to have a variation value within 1% by a negative feedback circuit, which is not illustrated. In addition, stable driving without electric discharge was confirmed by a discharge counter 76 during an evaluation of the stable drive of the X-ray generation apparatus 101.

The retention rate of the X-ray output of the X-ray generation apparatus 101 of this exemplary embodiment was 0.99. It was confirmed that no noticeable variation of the X-ray output was found in the X-ray generation apparatus 101 provided with the target 9 of this exemplary embodiment even after a long term driving history and a stable X-ray output intensity was obtained. When the X-ray generation apparatus 101 after the evaluation of the stability of the X-ray output intensity was disassembled and the anode 52 is taken out, no crack was found in the target layer 22 and the transmissive substrate 21.

Ten X-ray generation apparatus 101 prepared in this exemplary embodiment were prepared and an exposure test was performed 1000 times for each of the respective X-ray generation apparatus 101. Consequently, there was no X-ray generation apparatus 101 in which the anode current was lowered by 1% or more.

Comparative Example

A target, an anode, and the X-ray generation apparatus 101 were created as the transmitting type substrate 21 in the same manner as the first exemplary embodiment except that the monocrystal diamond was used. The monocrystal diamond used in this comparative example was observed by the electron backscattering diffraction method, and the fact that both of the surface configured to support the target layer and the opposed surface are dominated by a single monocrystal diamond was confirmed.

Figure 7:
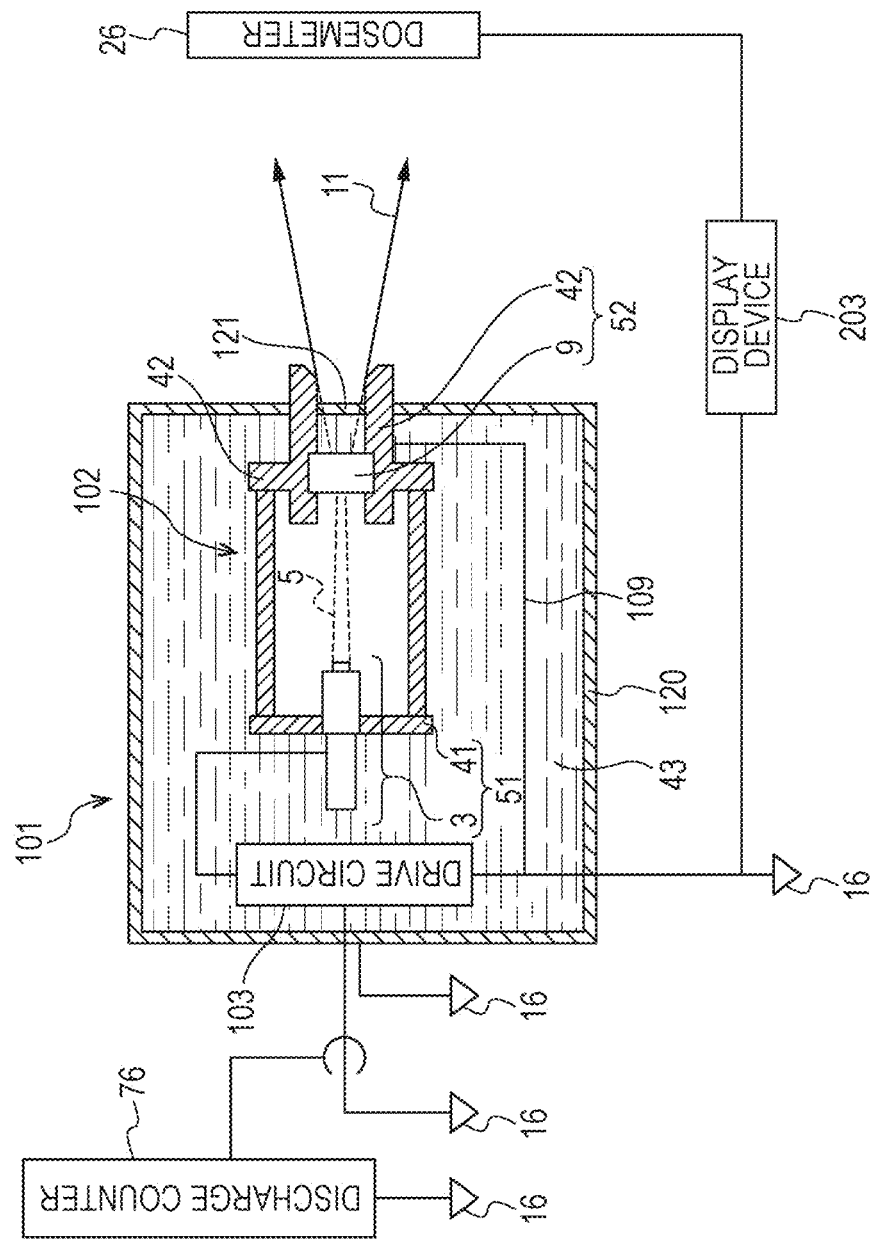
FIG. 7 is a configuration drawing illustrating an evaluation system 70 configured to evaluate an output stability of the X-ray generation apparatus.

In the same manner as the first exemplary embodiment, when the drive stability of the X-ray generation apparatus 101 by using the evaluation system 70 illustrated in FIG. 7 was evaluated, the retention rate of the X-ray output was on the order of 0.93.

Ten X-ray generation apparatus 101 prepared in the comparative example were prepared and an exposure test was performed 1000 times for each of the respective X-ray generation apparatus 101. Consequently, X-ray generation apparatus 101 in which the anode current was lowered by 10% or more were confirmed.

It was found that the X-ray generation tube of the X-ray generation apparatus in which lowering of the anode current was confirmed could not irradiate the target with the electron beam stably because vacuum leak was generated. When the X-ray generation tube in which anode current of the comparative example was lowered was taken out and the anode was observed, cracks was found in the wax material 48 and the target layer 22.

Fourth Embodiment

In this exemplary embodiment, an X-ray imaging system 60 illustrated in FIG. 5C was created by using the X-ray generation apparatus 101 described in the third exemplary embodiment.

In the X-ray imaging system 60 of this exemplary embodiment, with the provision of the X-ray generation apparatus 101 in which variations in X-ray output was restrained, an X-ray radiographing image having a high SN ratio was obtained.

Advantageous Effects of the Invention

According to this disclosure, even when the polycrystalline diamond is used in the transmissive substrate, a transmitting-type target in which generation of electric charge, lowering of the anode current, and X-ray output variations may not occur easily may be provided.

Also, by applying the transmitting-type target of this disclosure to the X-ray generation tube, highly reliable X-ray generating tube, X-ray generation apparatus, and X-ray imaging system in which generation of electric charge, lowering of an anode current, and X-ray output variations are alleviated are provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-253634 filed Dec. 6, 2013, No. 2013-253635 filed Dec. 6, 2013 and No. 2014-184462 filed Sep. 10, 2014, which are hereby incorporated by reference herein in their entirety.

What is claimed is:

1. A transmitting-type X-ray target comprising:
a target layer; and
a transmissive substrate configured to support the target layer,
wherein the transmissive substrate includes a first surface and a second surface facing each other and is formed of polycrystalline diamond,
wherein the first surface includes polycrystalline diamond having a first average crystal grain diameter which is smaller than a second average crystal grain diameter of polycrystalline diamond included in the second surface, and
wherein the target layer is supported by the first surface which includes the polycrystalline diamond having the first average crystal grain diameter, such that a grain diameter of the polycrystalline diamond increases from the first surface towards the second surface.

2. The transmitting-type target according to claim 1, wherein an average line density of grains of the polycrystalline diamond decreases from the first surface towards the second surface.

3. The transmitting-type target according to claim 1, wherein a ratio of the first average crystal grain diameter to the second average crystal grain diameter is 0.75 or lower.

4. The transmitting-type target according to claim 3, wherein the ratio of the first average crystal grain diameter to the second average crystal grain diameter is 0.2 or lower.

5. The transmitting-type target according to claim 1, wherein the first average crystal grain diameter is between 5 μm and 50 μm.

6. The transmitting-type target according to claim 1, wherein the second average crystal grain diameter is 100 μm or larger.

7. The transmitting-type target according to claim 1, wherein the transmissive substrate has column-shaped crystal grains extending in a substrate thickness direction from the first surface toward the second surface.

8. The transmitting-type target according to claim 1, wherein the target layer is supported by the second surface which includes the polycrystalline diamond having the second average crystal grain diameter.

9. The transmitting-type target according to claim 8, wherein the transmissive substrate is a self-contained diamond formed by being deposited on a seed crystal substrate by the chemical vapor-phase deposition method and removing the seed crystal substrate, wherein the first surface is a surface on the side of a growing surface side of the self-contained diamond, and the second surface is a seed crystal substrate side surface of the self-contained diamond.

10. The transmitting-type target according to claim 1, wherein a ratio of the second average crystal grain diameter to the first average crystal grain diameter is 1.3 or higher.

11. The transmitting-type target according to claim 10, wherein the ratio of the second average crystal grain diameter to the first average crystal grain diameter is 5 or higher.

12. The transmitting-type target according to claim 1, wherein a crystal grain field of the polycrystalline diamond forming the transmissive substrate contains sp2 bonding.

13. The transmitting-type target according to claim 12, wherein the sp2 bonding is determined by Raman shift of 1580 cm$^{-1}$ in a Raman spectrometry.

14. The transmitting-type target according to claim 1, wherein the polycrystalline diamond forming the transmissive substrate has a crystal grain diameter distribution in the substrate thickness direction, and
the average crystal grain diameter Dm is determined by the following expression when the crystal grain diameter distribution is sampled by the number of samples n in a crystal grain diameter axis $$D_m = \frac{\sum_{i=1}^{n}(D_i S_i)}{\sum_{i=1}^{n}(S_i)}$$

where a crystal grain diameter larger than a crystal grain diameter $D_{i-1}$ and not larger than $D_i$ is $D_i$, a cumulated surface area larger than the crystal grain diameter $D_{i-1}$ and not larger than $D_i$ is $S_i$, i is an integer from 1 to n, and a crystal grain diameter $D_0$ is an actual number not smaller than 0.

15. The transmitting-type target according to claim 14, wherein the average crystal grain diameter is determined by an electron backscattering diffraction method.

16. The transmitting-type target according to claim 1, wherein the transmissive substrate is self-contained diamond formed by being deposited on a seed crystal substrate by a chemical vapor-phase deposition method and removing the seed crystal substrate,
wherein the second surface is a surface on the side of a growing surface side of the self-contained diamond, and the first surface is a seed crystal substrate side surface of the self-contained diamond.

17. The transmitting-type target according to claim 1, wherein the target layer contains at least one metal material selected from a group consisting of tungsten, tantalum, and molybdenum.

18. The transmissive target according to claim 17, wherein the target layer contains a carbide of the selected metal material.

19. The transmitting-type target according to claim 1, wherein the thickness of the transmissive substrate is between 0.3 μm and 3 mm.

20. The transmitting-type target according to claim 1, wherein the thickness of the target layer is between 1 μm and 12 μm.

21. The transmitting-type target according to claim 1, wherein the crystal grain diameter of the polycrystalline diamond is smaller on the first surface that supports the target layer than the crystal grain diameter on the second surface opposed thereto.

22. An X-ray generation tube comprising:
transmitting-type target;
an electron emitting source having an electron emitting portion configured to emit electrons toward the target layer; and
an enclosure having an evacuated internal space,
wherein the electron emitting portion and the target layer are arranged in the internal space or on an inner surface of the enclosure, and
wherein transmitting-type target comprises:
a target layer; and
a transmissive substrate configured to support the target layer,
wherein the transmissive substrate includes a first surface and a second surface facing each other and is formed of polycrystalline diamond,
wherein the first surface includes polycrystalline diamond having a first average crystal grain diameter which is smaller than a second average crystal grain diameter of polycrystalline diamond included in the second surface, and
wherein the target layer is supported by the first surface which includes the polycrystalline diamond having the first average crystal grain diameter, such that a grain diameter of the polycrystalline diamond increases from the first surface towards the second surface.

23. An X-ray generation apparatus comprising:
an X-ray generation tube according to claim 22;
a drive circuit electrically connected to the target layer and the electron emitting portion respectively and configured to output a tube voltage applied between the target layer and the electron emitting portion.

24. An X-ray imaging system comprising:
an X-ray generation apparatus according to claim 23; and
an X-ray detector configured to detect an X-ray emitted from the X-ray generation apparatus and transmitted through a subject.

* * * * *